US011844651B2

(12) United States Patent
Honjo et al.

(10) Patent No.: US 11,844,651 B2
(45) Date of Patent: Dec. 19, 2023

(54) ANALYZING APPARATUS AND ANALYZING METHOD USING DISTRIBUTION INFORMATION

(71) Applicant: CANON MEDICAL SYSTEMS CORPORATION, Otawara (JP)

(72) Inventors: Yasunori Honjo, Utsunomiya (JP); Masaki Watanabe, Utsunomiya (JP); Yu Igarashi, Utsunomiya (JP); Tetsuya Kawagishi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 160 days.

(21) Appl. No.: 16/434,357

(22) Filed: Jun. 7, 2019

(65) Prior Publication Data
US 2019/0374204 A1 Dec. 12, 2019

(30) Foreign Application Priority Data
Jun. 8, 2018 (JP) .................................. 2018-110502

(51) Int. Cl.
*A61B 8/08* (2006.01)
*A61B 5/00* (2006.01)

(52) U.S. Cl.
CPC ............ *A61B 8/5207* (2013.01); *A61B 5/742* (2013.01); *A61B 8/085* (2013.01); *A61B 8/488* (2013.01)

(58) Field of Classification Search
CPC ....... A61B 8/5207; A61B 5/742; A61B 8/085; A61B 8/488
See application file for complete search history.

(56) References Cited

U.S. PATENT DOCUMENTS 5,749,831 A * 5/1998 Baker ...................... A61B 8/02
600/301
6,293,915 B1 * 9/2001 Amano .................. A61B 5/721
600/501
(Continued)

FOREIGN PATENT DOCUMENTS

JP       2006-288544 A      10/2006
JP       2008-080106 A       4/2008
(Continued)

OTHER PUBLICATIONS

K. Beach et al, "Carotid Artery Intraplaque Hemorrhage and Stenotic Velocity", Stroke, vol. 24, No. 2, pp. 314-319, Feb. 1993 (Year: 1993).*
(Continued)

*Primary Examiner* — Joel Lamprecht
*Assistant Examiner* — Nyrobi Celestine
(74) *Attorney, Agent, or Firm* — Oblon, McClelland, Maier & Neustadt, L.L.P.

(57) ABSTRACT

An analyzing apparatus according to an embodiment includes processing circuitry. The processing circuitry is configured to obtain pieces of Doppler image data in a time series rendering a blood flow in an analysis target formed in a blood vessel. The processing circuitry is configured to analyze the pieces of Doppler image data in the time series and to calculate an index value based on temporal changes in a first blood flow signal intensity level in a first region of interest including the blood flow in the analysis target.

28 Claims, 10 Drawing Sheets

(56) References Cited

U.S. PATENT DOCUMENTS

| | | | | |
|---|---|---|---|---|
| 7,338,452 | B2* | 3/2008 | Shiina | A61B 5/02007 600/467 |
| 7,727,153 | B2* | 6/2010 | Fritz | G06T 7/0012 600/449 |
| 8,740,798 | B2* | 6/2014 | Hamada | A61B 8/488 600/454 |
| 2003/0212336 | A1* | 11/2003 | Lee | A61B 5/7207 600/504 |
| 2006/0052704 | A1* | 3/2006 | Baba | A61B 8/488 600/453 |
| 2006/0241463 | A1* | 10/2006 | Shau | A61B 8/08 600/455 |
| 2007/0265508 | A1* | 11/2007 | Sheikhzadeh-Nadjar | A61B 7/04 607/9 |
| 2008/0281205 | A1* | 11/2008 | Naghavi | A61M 25/0662 600/458 |
| 2013/0066211 | A1* | 3/2013 | Konofagou | G01S 7/52057 600/450 |
| 2013/0137987 | A1* | 5/2013 | Abe | A61B 8/5207 600/454 |
| 2013/0204127 | A1* | 8/2013 | Hoogi | A61B 8/481 600/431 |
| 2014/0094666 | A1* | 4/2014 | Fine | A61B 5/7278 600/324 |
| 2014/0303499 | A1 | 10/2014 | Toma et al. | |
| 2015/0342565 | A1* | 12/2015 | Imamura | A61B 8/463 600/441 |
| 2016/0206287 | A1* | 7/2016 | Palti | A61B 8/5284 |
| 2016/0343134 | A1* | 11/2016 | Averkiou | G06F 18/22 |
| 2017/0071571 | A1* | 3/2017 | Lee | A61B 8/14 |
| 2017/0215838 | A1* | 8/2017 | Park | A61B 8/463 |
| 2017/0258438 | A1* | 9/2017 | Kanayama | A61B 5/055 |
| 2017/0367678 | A1* | 12/2017 | Sirtori | G16H 50/30 |
| 2018/0008236 | A1* | 1/2018 | Venkataraman | G06T 7/337 |
| 2019/0087958 | A1 | 3/2019 | Averkiou et al. | |

FOREIGN PATENT DOCUMENTS

| | | |
|---|---|---|
| JP | 2011-115457 A | 6/2011 |
| JP | 2014-158698 A | 9/2014 |
| JP | 2014-217745 | 11/2014 |
| JP | 2015-6260 | 1/2015 |
| JP | 2015-42213 | 3/2015 |
| JP | 2017-503603 | 2/2017 |
| WO | WO 2017/043442 A1 | 3/2017 |

OTHER PUBLICATIONS

S. Feinstein, "Contrast Ultrasound Imaging of the Carotid Artery Vasa Vasorum and Atherosclerotic Plaque Neovascularization", Journal of the American College of Cardiology, vol. 48, No. 2, pp. 236-243, Jul. 2006 (Year: 2006).*

F. Shah et al, "Contrast-enhanced ultrasound imaging of atherosclerotic carotid plaque neovascularization: a new surrogate marker of atherosclerosis?", Vascular Medicine, vol. 12, pp. 291-297, 2007 (Year: 2007).*

D. Staub et al, "Vasa Vasorum and Plaque Neovascularization on Contrast-Enhanced Carotid Ultrasound Imaging Correlates With Cardiovascular Disease and Past Cardiovascular Events", Stroke, vol. 41, No. 1, pp. 41-47, Jan. 2010 (Year: 2010).*

H. Kunte et al, "Detection of Unstable Carotid Plaque by Tissue Doppler Imaging and Contrast-Enhanced Ultrasound in a Patient with Recurrent Amaurosis Fugax", Case Reports in Vascular Medicine, vol. 2013, No. 354382, pp. 1-4, Jan. 2013 (Year: 2013).*

Chinese Office Action dated Oct. 28, 2021, issued in Chinese Patent Application No. 201910491247.0.

Office Action dated Jan. 17, 2023, in Japanese Patent Application No. 2019-106921, 5 pages.

* cited by examiner

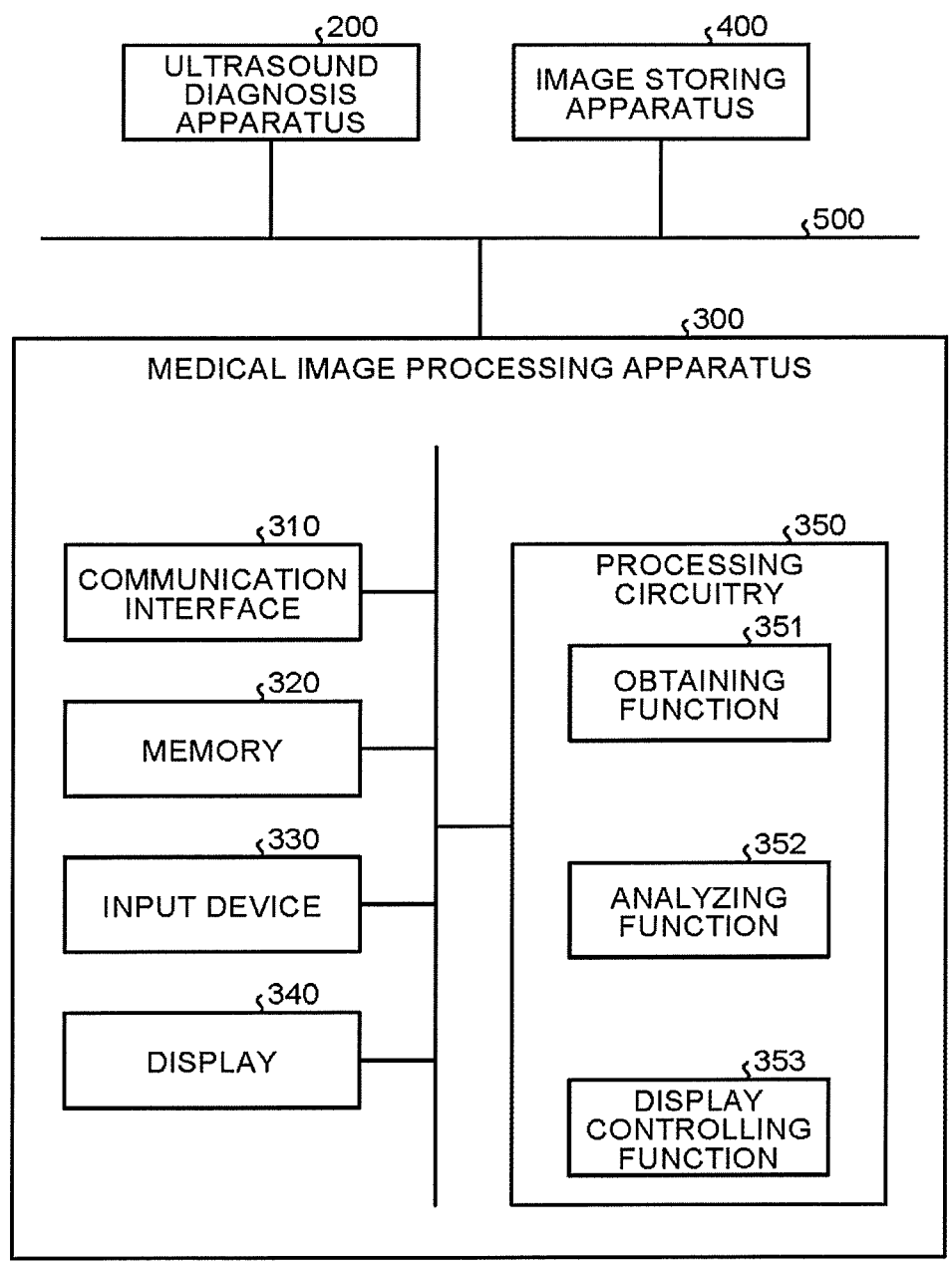

ANALYZING APPARATUS AND ANALYZING METHOD USING DISTRIBUTION INFORMATION

CROSS-REFERENCE TO RELATED APPLICATIONS

This application is based upon and claims the benefit of priority from Japanese Patent Application No. 2018-110502, filed on Jun. 8, 2018; the entire contents of which are incorporated herein by reference.

FIELD

Embodiments described herein relate generally to an analyzing apparatus and an analyzing method.

BACKGROUND

Carotid artery plaque is formed on the inner wall of the carotid artery and, when the plaque ruptures, blood clots are formed in the ruptured site. Those blood clots can be a cause of blockage of the carotid artery. Further, the blood clots may travel and clog a peripheral brain artery, which can be a cause of a cerebral infarction. In some situations, carotid artery plaque may come off during a procedure.

For these reasons, users such as medical doctors wish to be able to easily understand the state of such carotid artery plaque. Besides the state of carotid artery plaque, users also wish to be able to easily understand the state of a tumor when an examined subject is found to have one, as well as the state of a peripheral blood vessel or the like when an examined subject has diabetes.

BRIEF DESCRIPTION OF THE DRAWINGS

FIG. 11 is a diagram illustrating an exemplary configuration of a medical image processing apparatus according to a second embodiment.

DETAILED DESCRIPTION

An analyzing apparatus according to an embodiment includes processing circuitry. The processing circuitry is configured to obtain pieces of Doppler image data in a time series rendering a blood flow in an analysis target formed in a blood vessel. The processing circuitry is configured to analyze the pieces of Doppler image data in the time series and to calculate an index value based on temporal changes in a first blood flow signal intensity level in a first region of interest including the blood flow in the analysis target.

Exemplary embodiments of an analyzing apparatus and a computer program (hereinafter, "program") will be explained, with reference to the accompanying drawings. The explanation of each of the embodiments and the modification examples may similarly be applied to any other embodiment or modification example.

First Embodiment

Figure 1:
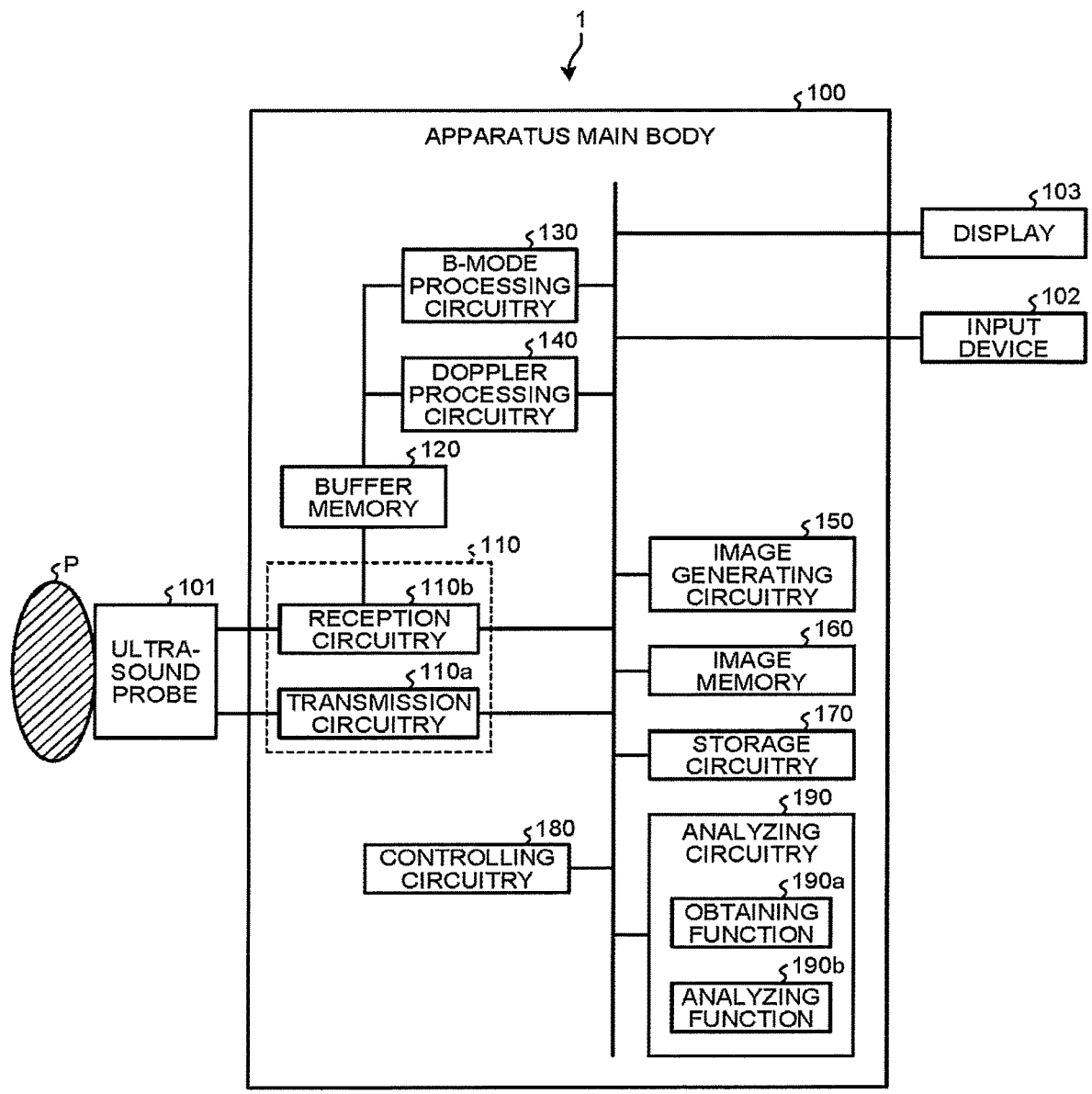
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, and a display 103. The ultrasound diagnosis apparatus 1 is an example of the analyzing apparatus.

The ultrasound probe 101 includes, for example, a plurality of elements such as piezoelectric transducer elements. Each of the plurality of elements is configured to generate an ultrasound wave on the basis of a drive signal supplied thereto from transmission circuitry 110a in transmission and reception circuitry 110 included in the apparatus main body 100. Further, the ultrasound probe 101 is configured to receive reflected waves from an examined subject (hereinafter "patient") P and to convert the received reflected waves into electrical signals. Further, for example, the ultrasound probe 101 includes a matching layer provided for the piezoelectric transducer elements, as well as a backing member or the like that prevents the ultrasound waves from propagating rearward from the piezoelectric transducer elements. The ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal by each of the plurality of elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction. Further, the ultrasound probe 101 outputs the reflected-wave signals to reception circuitry 110b (explained later) included in the transmission and reception circuitry 110.

The ultrasound probe 101 is provided so as to be attachable to and detachable from the apparatus main body 100. When a two-dimensional region in the patient P is to be scanned (a two-dimensional scan), an operator connects, for example, a one-dimensional (1D) array probe in which the plurality of piezoelectric transducer elements are arranged in a row to the apparatus main body 100, as the ultrasound probe 101. The 1D array probe may be a linear-type ultrasound probe, a convex-type ultrasound probe, a sector-type ultrasound probe, or the like. In contrast, when a three-dimensional region in the patient P is to be scanned (a three-dimensional scan), the operator connects, for example, a mechanical four-dimensional (4D) probe or a two-dimensional (2D) array probe to the apparatus main body 100, as the ultrasound probe 101. The mechanical 4D probe is capable of performing a two-dimensional scan by using the plurality of piezoelectric transducer elements arranged in a row such as those in the 1D array probe and is also capable of performing a three-dimensional scan by swinging the plurality of piezoelectric transducer elements at a predetermined angle (a swinging angle). Further, the 2D array probe is capable of performing a three-dimensional scan by using the plurality of piezoelectric transducer elements arranged in a matrix formation and is also capable of performing a two-dimensional scan by transmitting ultrasound waves in a converged manner.

The input device 102 is realized, for example, with input means such as a mouse, a keyboard, a button, a panel switch, a touch command screen, a foot switch, a trackball, a joystick, and/or the like. The input device 102 is configured to receive various types of setting requests from the operator of the ultrasound diagnosis apparatus 1 and to transfer the received various types of setting requests to the apparatus main body 100.

For example, the display 103 is configured to display a Graphical User Interface (GUI) used by the operator of the ultrasound diagnosis apparatus 1 for inputting the various types of setting requests through the input device 102 and to display an ultrasound image represented by ultrasound image data generated by the apparatus main body 100 and the like. The display 103 is realized by using a liquid crystal monitor, a Cathode Ray Tube (CRT) monitor, or the like.

The apparatus main body 100 is configured to generate the ultrasound image data on the basis of the reflected-wave signals received by the ultrasound probe 101. The ultrasound image data is an example of image data. The apparatus main body 100 is capable of generating two-dimensional ultrasound image data on the basis of reflected-wave data corresponding to a two-dimensional region of the patient P received by the ultrasound probe 101. Further, the apparatus main body 100 is also capable of generating three-dimensional ultrasound image data on the basis of reflected-wave data corresponding to a three-dimensional region of the patient P received by the ultrasound probe 101. As illustrated in FIG. 1, the apparatus main body 100 includes the transmission and reception circuitry 110, a buffer memory 120, B-mode processing circuitry 130, Doppler processing circuitry 140, image generating circuitry 150, an image memory 160, storage circuitry 170, controlling circuitry 180, and analyzing circuitry 190.

Under control of the controlling circuitry 180, the transmission and reception circuitry 110 is configured to cause ultrasound waves to be transmitted from the ultrasound probe 101 and to cause the ultrasound waves (the reflected-waves of the ultrasound waves) to be received by the ultrasound probe 101. In other words, the transmission and reception circuitry 110 performs an ultrasound scan (scanning with the ultrasound waves) via the ultrasound probe 101. The transmission and reception circuitry 110 includes the transmission circuitry 110a and the reception circuitry 110b.

Under the control of the controlling circuitry 180, the transmission circuitry 110a causes the ultrasound waves to be transmitted from the ultrasound probe 101. The transmission circuitry 110a includes a rate pulser generating circuit, a transmission delay circuit, and a transmission pulser, and is configured to supply the drive signal to the ultrasound probe 101. When scanning a two-dimensional region in the patient P, the transmission circuitry 110a causes an ultrasound beam used for scanning the two-dimensional region to be transmitted from the ultrasound probe 101. Further, when scanning a three-dimensional region in the patient P, the transmission circuitry 110a causes an ultrasound beam used for scanning the three-dimensional region to be transmitted from the ultrasound probe 101.

The rate pulser generating circuit is configured to repeatedly generate a rate pulse used for forming a transmission ultrasound wave (a transmission beam) at a predetermined rate frequency (a Pulse Repetition Frequency [PRF]). Voltage is applied to the transmission pulser, while the rate pulses have mutually-different transmission delay periods as a result of being routed through the transmission delay circuit. For example, the transmission delay circuit is configured to apply a transmission delay period that is required to converge the ultrasound waves generated by the ultrasound probe 101 into the form of a beam and to determine transmission directionality and that corresponds to each of the piezoelectric transducer elements, to each of the rate pulses generated by the rate pulser generating circuit. The transmission pulser is configured to apply the drive signal (a drive pulse) to the ultrasound probe 101 with timing based on the rate pulses. In this situation, by varying the transmission delay periods applied to the rate pulses, the transmission delay circuit arbitrarily adjusts the transmission directions of the ultrasound waves transmitted from the surfaces of the piezoelectric transducer elements.

After being transferred from the transmission pulser to the piezoelectric transducer elements in the ultrasound probe 101 via a cable, the drive pulse is converted from electric signals to mechanical vibration in the piezoelectric transducer elements. The ultrasound waves generated by the mechanical vibration are transmitted to the inside of the patient's body. In this situation, the ultrasound waves having the mutually-different transmission delay periods in correspondence with the piezoelectric transducer elements are converged and propagated into a predetermined direction.

The transmission circuitry 110a has a function that is able to instantly change the transmission frequency, the transmission drive voltage, and the like, for the purpose of executing a predetermined scan sequence under the control of the controlling circuitry 180. In particular, the function to change the transmission drive voltage is realized by using a linear-amplifier-type transmission circuit of which the value can be instantly switched or by using a mechanism configured to electrically switch between a plurality of power source units.

The reflected waves of the ultrasound waves transmitted by the ultrasound probe 101 reach the piezoelectric transducer elements provided in the ultrasound probe 101 and are subsequently converted from the mechanical vibration into electrical signals (the reflected-wave signals) in the piezoelectric transducer elements and are input to the reception circuitry 110b. The reception circuitry 110b includes a pre-amplifier, an Analog-to-Digital (A/D) converter, a quadrature detecting circuit, and the like and is configured to generate reflected-wave data by performing various types of processes on the reflected-wave signals received by the ultrasound probe 101. Further, the reception circuitry 110b is configured to store the generated reflected-wave data into the buffer memory 120.

The pre-amplifier is configured to amplify the reflected-wave signal for each of the channels and to perform a gain adjustment process (a gain correcting process). The A/D converter is configured to convert the gain-corrected reflected-wave signals into digital signals, by performing an A/D conversion on the gain-corrected reflected-wave signals. The quadrature detecting circuit is configured to convert the reflected-wave signals resulting from the A/D conversion into an In-phase signal (an I signal) and a Quadrature-phase signal (a Q signal) that are in a baseband. Further, the quadrature detecting circuit is configured to store the I signal and the Q signal (the IQ signals) into the buffer memory 120 as the reflected-wave data.

The reception circuitry 110b is configured to generate two-dimensional reflected-wave data from two-dimensional reflected-wave signals received by the ultrasound probe 101. Further, the reception circuitry 110b is configured to generate three-dimensional reflected-wave data from three-dimensional reflected-wave signals received by the ultrasound probe 101.

The buffer memory 120 is a memory configured to temporarily store therein the reflected-wave data generated by the transmission and reception circuitry 110. For example, the buffer memory 120 stores therein reflected-wave data corresponding to a number of frames or reflected-wave data corresponding to a number of volumes. For example, the buffer memory 120 stores therein reflected-wave data corresponding to a prescribed number of frames, under control of the reception circuitry 110b. Further, when reflected-wave data corresponding to one frame is newly generated by the reception circuitry 110b while the buffer memory 120 is in the state of storing therein the reflected-wave data corresponding to the prescribed number of frames, the buffer memory 120 discards the reflected-wave data corresponding to the one frame that was generated earliest and stores therein the newly-generated reflected-wave data corresponding to the one frame, under the control of the reception circuitry 110b. For example, the buffer memory 120 is realized by using a semiconductor memory element such as a Random Access Memory (RAM), a flash memory, or the like.

The B-mode processing circuitry 130 and the Doppler processing circuitry 140 are signal processing units configured to read any of the reflected-wave data from the buffer memory 120 and to perform various types of signal processing processes on the read reflected-wave data.

The B-mode processing circuitry 130 is configured to generate data (B-mode data) in which the signal intensity (amplitude intensity) corresponding to each sampling point is expressed by a degree of brightness, by performing a logarithmic amplification and an envelope detecting process or the like on the reflected-wave data read from the buffer memory 120. The B-mode processing circuitry 130 is configured to output the generated B-mode data to the image generating circuitry 150. The B-mode processing circuitry 130 is realized by using a processor, for example.

By performing a frequency analysis on the reflect-wave data read from the buffer memory 120, the Doppler processing circuitry 140 is configured to extract motion information of moving members (a blood flow, a tissue, a contrast agent echo component, and the like) based on the Doppler effect and to generate data (Doppler data) indicating the extracted motion information. For example, as the motion information of the moving members, the Doppler processing circuitry 140 extracts an average velocity value, an average dispersion value, an average power value, and the like from multiple points and generates the Doppler data indicating the extracted motion information of the moving members. The Doppler processing circuitry 140 is configured to output the generated Doppler data to the image generating circuitry 150.

By using the function of the Doppler processing circuitry 140 described above, the ultrasound diagnosis apparatus 1 according to the first embodiment is capable of implementing a color Doppler method that may be called a Color Flow Mapping (CFM) method. According to the color flow mapping method, ultrasound waves are transmitted and received multiple times on a plurality of scanning lines. Further, according to the color flow mapping method, by applying a Moving Target Indicator (MTI) filter to a data sequence in the same position, a signal derived from a blood flow is extracted from the data sequence in the same position, while suppressing a signal (clutter signal) derived from a stationary tissue or a slow-moving tissue. Further, according to the color flow mapping method, blood flow information such as an average velocity value of the blood flow, an average dispersion value of the blood flow, and an average power value of the blood flow are estimated from the blood flow signal. Further, according to the color flow mapping method, Doppler data indicating the estimated blood flow information is generated. Further, the image generating circuitry 150 (explained later) is configured to generate Doppler image data (color Doppler image data) in which a distribution of estimated results of the blood flow information indicated by the Doppler data is two-dimensionally displayed in color, for example. Alternatively, the image generating circuitry 150 may generate Doppler image data in which a distribution of estimated results of the blood flow information is displayed in a gray scale, for example. After that, the display 103 displays the Doppler image represented by the Doppler image data.

As the MTI filter, the Doppler processing circuitry 140 according to the present embodiment uses an adaptive MTI filter configured to vary a coefficient in accordance with an input signal. For example, as the adaptive MTI filter, the Doppler processing circuitry 140 uses a filter called "Eigenvector Regression Filter". In the following sections, such an "Eigenvector Regression Filter" serving as an adaptive MTI filter that uses eigenvectors will be referred to as an "eigenvector MTI filter".

The eigenvector MTI filter is configured to calculate an eigenvector from a correlation matrix and to calculate a coefficient to be used in the clutter component suppressing process from the calculated eigenvector. This method is an application of a method used in a main component analysis, a Karhunen-Loeve transform, or an eigenspace method.

The Doppler processing circuitry 140 according to the first embodiment that uses the eigenvector MTI filter is configured to calculate a correlation matrix of the first region from the data sequence including consecutive pieces of reflected-wave data in mutually the same position (the same sampling point). Further, the Doppler processing circuitry 140 is configured to calculate eigenvalues of the correlation matrix and eigenvectors corresponding to the eigenvalues. Further, the Doppler processing circuitry 140 is configured to calculate a matrix obtained by reducing the rank of a matrix in which the eigenvectors are arranged on the basis of magnitudes of the eigenvalues, as a filter matrix used for suppressing the clutter component.

Further, by using the filter matrix, the Doppler processing circuitry 140 is configured to specify a data sequence extracting a blood flow signal derived from the blood flow while suppressing the clutter component, from the data sequence including the consecutive pieces of reflected-wave data in mutually the same position (the same sampling point). In other words, the Doppler processing circuitry 140 is configured to extract the blood flow signal from the data sequence including the consecutive pieces of reflected-wave data in mutually the same position by using the filter matrix and to specify the data sequence based on the blood flow signal. Further, the Doppler processing circuitry 140 is configured to estimate the blood flow information by performing a calculation such as an autocorrelation calculation by using the specified data sequence. Further, the Doppler processing circuitry 140 is configured to output Doppler data indicating the estimated blood flow information, to the image generating circuitry 150. Specific processes performed by the Doppler processing circuitry 140 according to the first embodiment will be explained in detail later. The Doppler processing circuitry 140 is realized by using, for example, a processor.

The B-mode processing circuitry 130 and the Doppler processing circuitry 140 are capable of processing both two-dimensional reflected-wave data and three-dimensional reflected-wave data.

The image generating circuitry 150 is configured to generate the ultrasound image data from the data output by the B-mode processing circuitry 130 and the Doppler processing circuitry 140. The image generating circuitry 150 is configured to generate two-dimensional B-mode image data in which intensities of reflected waves are expressed with degrees of brightness, from the two-dimensional B-mode data generated by the B-mode processing circuitry 130. Further, the image generating circuitry 150 is configured to generate two-dimensional Doppler image data in which the blood flow information is rendered in a picture, from the two-dimensional Doppler data generated by the Doppler processing circuitry 140. The two-dimensional Doppler image data is velocity image data, dispersion image data, power image data, or image data combining together any of these types of image data. From the Doppler data serving as the blood flow information, the image generating circuitry 150 is configured to generate, as Doppler image data, blood flow image data in which the blood flow information is displayed in color or blood flow image data in which the blood flow information is displayed in a gray scale. The image generating circuitry 150 is realized by using a processor.

In this situation, generally speaking, the image generating circuitry 150 converts (by performing a scan convert process) a scanning line signal sequence from an ultrasound scan into a scanning line signal sequence in a video format used by, for example, television and generates display-purpose ultrasound image data. For example, the image generating circuitry 150 generates the display-purpose ultrasound image data by performing a coordinate transformation process compliant with the ultrasound scanning mode used by the ultrasound probe 101. Further, as various types of image processing processes besides the scan convert process, the image generating circuitry 150 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuitry 150 combines text information of various types of parameters, scale graduations, body marks, and the like with the ultrasound image data.

Further, the image generating circuitry 150 generates three-dimensional B-mode image data by performing a coordinate transformation process on the three-dimensional B-mode data generated by the B-mode processing circuitry 130. Further, the image generating circuitry 150 generates three-dimensional Doppler image data by performing a coordinate transformation process on the three-dimensional Doppler Data generated by the Doppler processing circuitry 140. In other words, the image generating circuitry 150 is configured to generate the "three dimensional B-mode image data and three-dimensional Doppler image data" as "three-dimensional ultrasound image data (volume data)". Further, the image generating circuitry 150 is configured to perform various rendering processes on the volume data to generate various types of two-dimensional image data used for displaying the volume data on the display 103.

Examples of the rendering process performed by the image generating circuitry 150 include a process of generating MPR image data from the volume data by implementing a Multi Planar Reconstruction (MPR) method, for example. Another example of the rendering process performed by the image generating circuitry 150 is a Volume Rendering (VR) process by which two-dimensional image data reflecting three-dimensional information is generated.

The B-mode data and the Doppler data are each ultrasound image data before the scan convert process. The data generated by the image generating circuitry 150 is the display-purpose ultrasound image data after the scan convert process. The B-mode data and the Doppler data may be referred to as raw data. Further, both the Doppler data and the Doppler image data may each be referred to as Doppler image data.

The image memory 160 is a memory configured to store therein various types of image data generated by the image generating circuitry 150. Further, the image memory 160 is also configured to store therein any of the data generated by the B-mode processing circuitry 130 and the Doppler processing circuitry 140. After a diagnosis process, for example, the operator is able to invoke any of the B-mode data and the Doppler data stored in the image memory 160. The invoked B-mode data and Doppler data can serve as display-purpose ultrasound image data after being routed through the image generating circuitry 150. For example, the image memory 160 is realized by using a semiconductor memory element such as a RAM, a flash memory, or the like, or a hard disk or an optical disk.

The storage circuitry 170 is configured to store therein control programs for performing ultrasound wave transmissions and receptions, image processing processes, and display processes, other various types of programs, diagnosis information (e.g., patients' IDs, medical doctors' observations), diagnosis protocols, and various types of data such as various types of body marks or the like. Further, the storage circuitry 170 may also be used, as necessary, for saving therein any of the data stored in the image memory 160, and the like. For example, the storage circuitry 170 is realized by using a semiconductor memory element such as a flash memory, a hard disk, or an optical disk.

The controlling circuitry 180 is configured to control the entirety of processes performed by the ultrasound diagnosis apparatus 1. More specifically, on the basis of the various types of setting requests input from the operator via the input device 102 and the various types of control programs and various types of data read from the storage circuitry 170, the controlling circuitry 180 controls processes performed by the transmission and reception circuitry 110, the B-mode processing circuitry 130, the Doppler processing circuitry 140, the image generating circuitry 150, and the analyzing circuitry 190. Further, the controlling circuitry 180 has a display controlling function of controlling the display 103 so as to display any of the ultrasound images represented by the various types of display-purpose ultrasound image data stored in the image memory 160. The controlling circuitry 180 is an example of a display controlling unit. The controlling circuitry 180 may be realized by using a processor, for example.

The analyzing circuitry 190 is configured to perform various types of analyses. As illustrated in FIG. 1, the analyzing circuitry 190 includes an obtaining function 190a and an analyzing function 190b. In this situation, for example, processing functions of the constituent elements of the analyzing circuitry 190 illustrated in FIG. 1, namely, the obtaining function 190a and the analyzing function 190b, are recorded in the storage circuitry 170 in the form of computer-executable programs. The analyzing circuitry 190 realizes the functions corresponding to the programs by reading the programs from the storage circuitry 170 and executing the read programs. In other words, the analyzing circuitry 190 that has read the programs has the functions illustrated within the analyzing circuitry 190 illustrated in FIG. 1. The analyzing circuitry 190 is realized by using a processor, for example.

Alternatively, all the processing functions of the obtaining function 190a and the analyzing function 190b may be recorded in the storage circuitry 170 in the form of a single computer-executable program. In that situation, the analyzing circuitry 190 realizes the obtaining function 190a and the analyzing function 190b corresponding to the programs by reading the program from the storage circuitry 170 and executing the read program.

In another example, all the processing functions, namely, the obtaining function 190a, the analyzing function 190b, and the display controlling function of the controlling circuitry 180 may be recorded in the storage circuitry 170 in the form of a single computer-executable program. In that situation, the controlling circuitry 180 and the analyzing circuitry 190 are integrated in single processing circuitry, so that the processing circuitry realizes the obtaining function 190a, the analyzing function 190b, and the display controlling function corresponding to the program by reading the program from the storage circuitry 170 and executing the read program. The processing circuitry is realized by using a processor, for example.

The obtaining function 190a is an example of an obtaining unit. The analyzing function 190b is an example of an analyzing unit. The display controlling function is an example of a display controlling unit.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the one or more programs saved in the storage circuitry 170. In this situation, instead of saving the programs in the storage circuitry 170, it is also acceptable to directly incorporate the programs in the circuitries of the processors. In that situation, the processors realize the functions thereof by reading and executing the programs incorporated in the circuitries thereof. The processors in the present embodiment do not each necessarily have to be structured as single circuitry. It is also acceptable to structure one processor by combining together a plurality of independent circuitries so as to realize the functions thereof. Further, it is also acceptable to integrate two or more of the constituent elements in FIG. 1 into one processor so as to realize the functions thereof.

An overall configuration of the ultrasound diagnosis apparatus 1 according to the first embodiment has thus been explained. To generate information that makes it possible for a user to easily judge the state of carotid artery plaque (plaque), the ultrasound diagnosis apparatus 1 performs various types of processes as explained below.

The ultrasound diagnosis apparatus 1 according to the present embodiment is configured to acquire a blood flow image indicating blood flow information in the plaque and blood flow information in the carotid artery and a tissue image indicating a tissue shape. In this situation, the blood flow image is a Doppler image represented by Doppler image data. The tissue image is a B-mode image represented by B-mode image data serving as tissue image data.

To perform the acquisition, the transmission and reception circuitry 110 is configured to perform an ultrasound scan (a first ultrasound scan) to acquire the Doppler image data in a Doppler mode and to perform an ultrasound scan (a second ultrasound scan) to acquire the B-mode image data in a B-mode. The first ultrasound scan is an ultrasound scan performed on a region (a first region) including plaque formed in the carotid artery of the patient P, to obtain blood flow information (the blood flow information in the plaque and the blood flow information in the carotid artery) within the first region. The carotid artery is an example of a blood vessel. The second ultrasound scan is an ultrasound scan is an ultrasound scan performed to obtain information about the tissue shape in a region (a second region) inside the patient P.

It is sufficient when the first region and the second region at least partially overlap with each other. The area of the first region and the area of the second region may be the same. The area of the first region may be smaller than the area of the second region. Conversely, the area of the second region may be smaller than the area of the first region.

In the first embodiment, the transmission and reception circuitry 110 performs, via the ultrasound probe 101, the first ultrasound scans and the second ultrasound scans so as to alternate. Further, as for the scanning mode of the first ultrasound scans, the ultrasound wave is transmitted and received once with respect to each of the scanning lines, in the first region formed with the plurality of scanning lines. By using this scanning mode, it is possible to improve the framerate. In the following sections, the first ultrasound scans will be referred to as "high framerate ultrasound scans". The CFM method implemented by performing the "high framerate ultrasound scans" will be referred to as a "high framerate method".

Incidentally, according to an ordinary color Doppler method, ultrasound wave transmission and reception is performed multiple times in the same direction, so as to extract a blood flow signal from the signal received in this manner. The data sequence including reflected-wave signals (reflected-wave data) from mutually the same position obtained from the ultrasound wave transmissions and receptions performed in this manner is called a "packet". A packet size denotes the number of times the ultrasound wave transmission and reception is performed in the same direction to obtain the blood flow information corresponding to one frame. The packet size in a generally-used color Doppler method is approximately in the range of 5 to 16. Levels of performance of eigenvector MTI filters are improved when the packet size is larger. However, when the packet size is increased, the framerate becomes lower.

In contrast, according to the high framerate method, it is possible to perform processes on data sequences in the same position in different frames, in the frame direction (time direction). For example, according to the high framerate method, it is possible to perform the MTI filtering process as a process performed on data of an infinite length, in contrast to the data processing having a finite length of the packet. As a result, by using the high framerate method, it is possible to improve the level of performance of the MTI filter. Consequently, it is possible to estimate blood flow information about a blood flow having a lower flowrate, to estimate blood flow information about a blood flow in a small blood vessel, and to display a blood flow image indicating blood flow information at a higher framerate. For example, by using the high framerate method, it is possible to estimate blood flow information about a small blood flow in the plaque, in addition to blood flow information about the blood flow in the carotid artery.

Together with the first ultrasound scans realized with the high framerate ultrasound scans, the controlling circuitry 180 according to the first embodiment is configured to cause the second ultrasound scans to be performed in a scanning mode explained below.

The controlling circuitry 180 divides the second region into a plurality of segmented regions and causes the ultrasound probe 101 to perform the second ultrasound scan on each of the plurality of segmented regions in a time-division manner between the first ultrasound scans. In other words, the transmission and reception circuitry 110 is configured to perform, via the ultrasound probe 101, the first ultrasound scans and the second ultrasound scans so as to alternate, the second ultrasound scans being performed on the plurality of segmented regions obtained by dividing the second region into the segments. Accordingly, in the first embodiment, the transmission and reception circuitry 110 performs each of the second ultrasound scans between the first ultrasound scans so as to complete the second ultrasound scans corresponding to one frame, during the time period when the first ultrasound scans corresponding to a number of frames are performed. By using this scanning mode, the ultrasound diagnosis apparatus 1 according to the first embodiment is able to set ultrasound wave transmission and reception conditions (image quality conditions) for the first ultrasound scans and for the second ultrasound scans, independently of each other. Alternatively, the controlling circuitry 180 may perform the second ultrasound scans without using the time-division scheme. In other words, as the second ultrasound scans, the controlling circuitry 180 may cause the ultrasound probe 101 to perform an ultrasound scan on the entire second region, instead of each segmented region.

Figure 2:
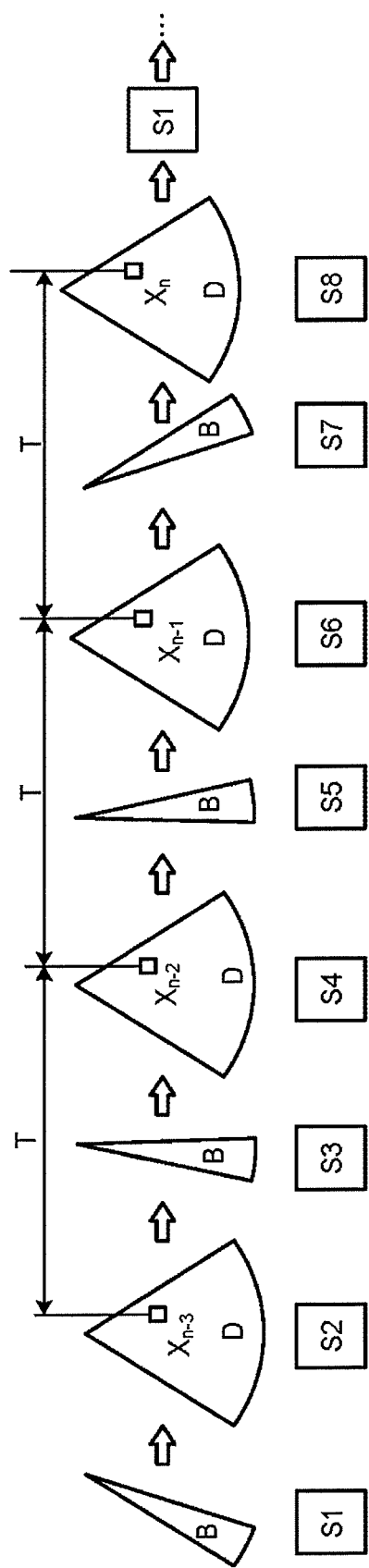
FIG. 2 is a drawing for explaining examples of first ultrasound scans and second ultrasound scans according to the first embodiment.
Figure 3:
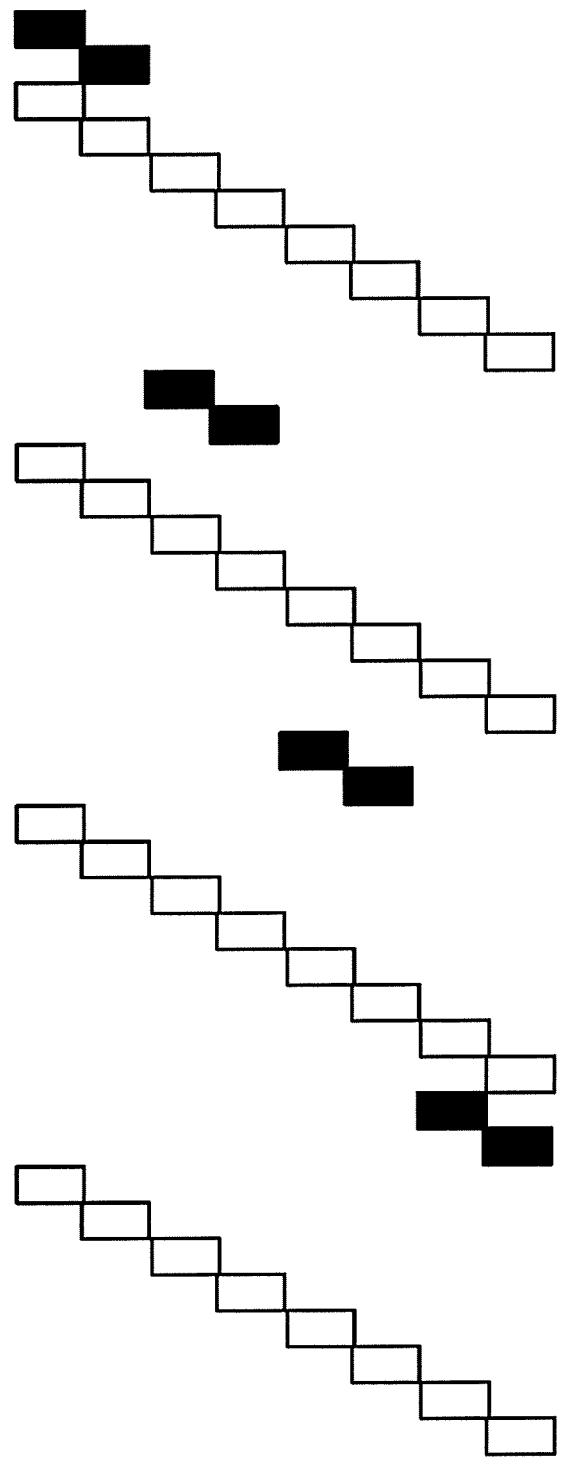
FIG. 3 is another drawing for explaining the examples of the first ultrasound scans and the second ultrasound scans according to the first embodiment.

Next, the first ultrasound scans and the second ultrasound scans will be explained. FIGS. 2 and 3 are drawings for explaining examples of the first ultrasound scans and the second ultrasound scans according to the first embodiment. As illustrated in FIG. 2, on the basis of an instruction from the operator or information in an initial setting or the like, the controlling circuitry 180 divides the second region into four segmented regions (first to fourth segmented regions). In FIG. 2, the letter "B" indicates each of the segmented regions on which the second ultrasound scans are performed by using a transmission and reception condition in the B-mode. Each of the segmented regions is formed with at least one scanning line.

For example, the transmission and reception circuitry 110 transmits an ultrasound wave with respect to each of the scanning lines structuring each of the segmented regions, so that the B-mode processing circuitry 130 generates B-mode data on the basis of reflected-wave data based on a reflected wave of the ultrasound wave.

Further, in FIG. 2, the letter "D" denotes the first region on which the first ultrasound scans are performed by using a transmission and reception condition for a color flow mapping process. For example, the letter "D" in FIG. 2 denotes a range in which an ultrasound scan is performed by implementing the high framerate method described above. In other words, in the first ultrasound scans, the ultrasound wave is transmitted and received once with respect to each of the scanning lines, unlike the generally-used color Doppler method by which an ultrasound wave is transmitted multiple times in the same direction to receive reflected-waves multiple times. As the first ultrasound scans, the transmission and reception circuitry 110 transmits and receives the ultrasound wave once with respect to each of the plurality of scanning lines forming the first region. In this manner, the ultrasound scan is performed on the basis of the method (the high framerate method) by which the blood flow information is obtained by using the reflected waves corresponding to the plurality of frames.

As illustrated in FIG. 2, the transmission and reception circuitry 110 at first performs the second ultrasound scans on the first segmented region (step S1) and performs the first ultrasound scans on the first region (corresponding to one frame) (step S2). Further, the transmission and reception circuitry 110 performs the second ultrasound scans on the second segmented region (step S3) and performs the first ultrasound scans on the first region (step S4). After that, the transmission and reception circuitry 110 performs the second ultrasound scans on the third segmented region (step S5) and performs the first ultrasound scans on the first region (step S6). Subsequently, the transmission and reception circuitry 110 performs the second ultrasound scans on the fourth segmented region (step S7), performs the first ultrasound scans on the first region (step S8), and returns to step S1.

In this situation, as illustrated in FIG. 2, the controlling circuitry 180 controlling the first ultrasound scans performed by the transmission and reception circuitry 110 arranges the intervals at which the first ultrasound scans are performed to be regular intervals. In other words, a "point X" on a "certain scanning line" in the first region is scanned once in each of the first ultrasound scans performed at steps S2, S4, S6, and S8 in FIG. 2, while the scanning intervals thereof is controlled to be constant as "T". For example, the controlling circuitry 180 arranges the intervals at which the first ultrasound scans are performed to be regular intervals, by keeping the time periods required by the second ultrasound scans to be the same as one another. For example, the controlling circuitry 180 exercises control so that the time periods required by the second ultrasound scans performed at steps S1, S3, S5, and S7 in FIG. 2 to be the same length of time. The controlling circuitry 180 arranges the sizes of the segmented regions obtained by dividing the second region, the number of scanning lines, the density and the depth of the scanning lines, and the like to be the same as one another. For example, when the numbers of scanning lines are the same, the time periods required by the second ultrasound scans will be the same as one another. The Doppler processing circuitry 140 is configured to output blood flow information of the "point X" by performing the process described below on a data sequence ("$X_{n-3}$, $X_{n-2}$, $X_{n-1}$, $X_n$, . . . " illustrated in FIG. 2) in the same position within the first region among the frames. In the method described above, the controlling circuitry 180 having the display controlling function updates one part of the tissue image corresponding to a segmented region at the intervals "T", instead of updating the tissue image displayed on the display 103 at the intervals of "4T".

In a conventional color Doppler process, the "MTI filtering process" and the "process of estimating velocity, dispersion, and power" are performed on a data sequence closed within the packet. For this reason, in the conventional color Doppler process, it is possible to output only one piece of blood flow information with respect to one packet. In contrast, in the color Doppler process performed in the scanning mode implementing the high framerate method, there is no concept of packets in the scans themselves. Accordingly, in the color Doppler process performed in the scanning mode described above, it is possible to arbitrarily change the data length of the data sequence used in the process performed for outputting one piece of blood flow information.

Further, in the color Doppler process performed in the scanning mode described above, it is possible to arrange a data sequence used in the process performed for outputting blood flow information in a former temporal phase to overlap with a data sequence used in the process performed for outputting blood flow information in a latter temporal phase.

This aspect will be explained with reference to FIG. 3. FIG. 3 illustrates an example in which the first region and the second region represent mutually the same scanned range, while the scanned range is formed with eight scanning lines, namely, first to eighth scanning lines. Further, in FIG. 3, the eight scanning lines are numbered as "1, 2, 3, 4, 5, 6, 7, and 8" along the azimuth direction (the direction in which the transducer elements are arranged in the ultrasound probe 101). Further, in FIG. 3, the second ultrasound scans are indicated with black rectangles, while the first ultrasound scans are indicated with white rectangles. FIG. 3 is a drawing illustrating the example in which the scanned range illustrated in FIG. 2 is scanned in the scanning mode according to the first embodiment. More specifically, FIG. 3 illustrates the example in which the first region illustrated in FIG. 2 is formed with eight scanning lines, while segmented regions obtained by dividing the second region, which is the same region as the first region, into four segments are each formed with two scanning lines.

During the scans illustrated in FIG. 3, the second ultrasound scans are performed on the first scanning line and the second scanning line in the stated order. After the second ultrasound scan is performed on the second scanning line, the first ultrasound scans are sequentially performed on the first to the eighth scanning lines in the stated order (the first ultrasound scans for the first time).

Subsequently, after the first ultrasound scans performed for the first time, the second ultrasound scans are performed on the third scanning line and the fourth scanning line in the state order. After the second ultrasound scan is performed on the fourth scanning line, the first ultrasound scans are performed again on the first to the eighth scanning line in the stated order (the first ultrasound scans for the second time).

Subsequently, after the second ultrasound scans are performed on the fifth scanning line and the sixth scanning line in the stated order, the first ultrasound scans are performed again on the first to the eighth scanning lines in the stated order (the first ultrasound scans for the third time).

Subsequently, after the second ultrasound scans are performed on the seventh scanning line and the eighth scanning line in the stated order, the first ultrasound scans are performed again on the first to the eighth scanning lines in the stated order (the first ultrasound scans for the fourth time). Also after the first ultrasound scans are performed for the fourth time, the second ultrasound scans and the first ultrasound scans are performed so as to alternate in a similar manner. In other words, in the first embodiment, the transmission and reception circuitry 110 performs the first ultrasound scans on the first region and the second ultrasound scans on parts (the segmented regions) of the second region so as to alternate.

Next, an example will be explained in which the data length of the data sequence is set to "4", while the number of overlapping data sequences (hereinafter "overlapping number") between displayed frames is set to "3". In this situation, the Doppler processing circuitry 140 generates Doppler data for the first frame, from the reflected-wave data acquired in the first ultrasound scans performed for the first time up to the fourth time. In other words, the Doppler processing circuitry 140 generates the Doppler data for the first frame from the reflected-wave data acquired in the first ultrasound scans corresponding to the four times, which correspond to the data length "4" of the data sequence. The Doppler data is data from which the Doppler image data (the blood flow image data) is to be generated. Further, from the Doppler data for the first frame, the image generating circuitry 150 generates Doppler image data of the first frame. Subsequently, the controlling circuitry 180 causes the display 103 to display a Doppler image of the first frame represented by the Doppler image data of the first frame.

Subsequently, the Doppler processing circuitry 140 generates Doppler data for the second frame, from the reflected-wave data acquired in the first ultrasound scans performed for the second time up to the fifth time. In this situation, the reflected-wave data acquired in the first ultrasound scans performed for the second time up to the fifth time and the reflected-wave data acquired in the first ultrasound scans performed for the first time up to the fourth time described above overlap with each other by the reflected-wave data acquired in the first ultrasound scans performed for the second time up to the fourth time. In other words, the two pieces of reflected-wave data overlap with each other by the number corresponding to the overlapping number "3".

Subsequently, from the Doppler data for the second frame, Doppler image data of the second frame is generated. After that, the display 103 displays a Doppler image of the second frame represented by the Doppler image data of the second frame. Similarly, from the reflected-wave data acquired in the first ultrasound scans performed for the third time up to the sixth time, Doppler data for the third frame is generated. In other words, from the reflected-wave data acquired in the first ultrasound scans performed for an N-th time up to an (N+3)-th time, Doppler data for an N-th frame is generated, where N is a positive integer.

In the example illustrated in FIG. 3, the second ultrasound scans corresponding to one frame are completed when the first ultrasound scans corresponding to the four frames are completed. In the example illustrated in FIG. 3, the display mode is such that, while one frame of the blood flow image is displayed, images in the segmented regions (parts of the tissue image) obtained by dividing the second region into the four segments are updated. In this situation, the controlling circuitry 180 superimposes the blood flow image on the tissue image and causes the display 103 to display the tissue image and the blood flow image.

Next, an example of the first ultrasound scans will be explained. In the first ultrasound scans, the transmission and reception circuitry 110 performs, via the ultrasound probe 101, the ultrasound wave transmission and reception only once with respect to each of the scanning lines. More specifically, as the first ultrasound scans, the transmission and reception circuitry 110 transmits an ultrasound wave once with respect to each of the plurality of scanning lines forming the first region and receives reflected waves of the ultrasound waves. Further, with respect to each of the scanning lines, the transmission and reception circuitry 110 generates reflected-wave data based on the reflected waves of the ultrasound waves. Further, the transmission and reception circuitry 110 repeatedly performs the process of generating reflected-wave data in this manner as many times as a plurality of frames. After that, the Doppler processing circuitry 140 estimates blood flow information on the basis of the reflected-wave data based on the reflected waves of the ultrasound waves corresponding to the plurality of frames. Further, the Doppler processing circuitry 140 generates Doppler data indicating the estimated blood flow information. After that, on the basis of the Doppler data, the image generating circuitry 150 generates Doppler image data.

Next, an example of a method for generating an MTI filter matrix according to the first embodiment will be explained. The Doppler processing circuitry 140 at first calculates a correlation matrix of a scanned range, from a data sequence including consecutive pieces of reflected-wave data in mutually the same position acquired by repeating the scanning mode in which the ultrasound wave is transmitted and received once with respect to each of the scanning lines in the first region formed by the plurality of scanning lines.

More specifically, the Doppler processing circuitry 140 calculates a correlation matrix "$R_{xx}$" by using Expression (1) presented below.

$$R_{xx} = \frac{1}{M} \sum_{m=1}^{M} X_m X_m^H \qquad (1)$$

In this situation, "$x_m$" in Expression (1) is a column vector expressing the data sequence in a position "m". The length "L" of the column vector "$x_m$" is a data length used for the calculation to estimate the Doppler data (the blood flow information) in one frame. For example, in the example in FIG. 3, "L" is equal to "4". Further, in Expression (1), "$x_m^H$" denotes a transposed matrix of a matrix taking complex conjugates of the elements of "$x_m$".

In this situation, the position "m" denotes the position of a sampling point set in the entire space in which the high framerate ultrasound scan is performed. The position "m" is expressed in a two-dimensional coordinate system when a two-dimensional scan is performed and is expressed in a three-dimensional coordinate system when a three-dimensional scan is performed. Further, "M" in Expression (1) denotes the total quantity of "m".

In other words, by using Expression (1), the Doppler processing circuitry 140 is configured to calculate an autocorrelation matrix of the data sequence at each of a plurality of sampling points and to calculate an average of autocorrelation matrices of the plurality of sampling points. As a result, the Doppler processing circuitry 140 calculates a correlation matrix of the first region. From Expression (1), the correlation matrix "$R_{xx}$" is a matrix having L lines and L columns. In this situation, as explained above, it is possible to arbitrarily change the data length "L" of the data sequence of which the correlation matrix is calculated. Further, the data sequence of which the correlation matrix is calculated may be set so as to overlap between displayed frames.

Further, the Doppler processing circuitry 140 calculates eigenvalues of the correlation matrix and eigenvectors corresponding to the eigenvalues. In other words, the Doppler processing circuitry 140 calculates L sets of eigenvalues and eigenvectors from the correlation matrix "$R_{xx}$". Further, the Doppler processing circuitry 140 sets a matrix "V" by arranging the "L" eigenvectors on the basis of the magnitudes of the eigenvalues. After that, the Doppler processing circuitry 140 calculates a matrix obtained by reducing the rank of the matrix "V", as an MTI filter matrix used for suppressing the clutter component. The Doppler processing circuitry 140 obtains the matrix "V" by using the "L" eigenvectors as "L" column vectors and arranging the "L" column vectors in descending order of the eigenvalues thereof and further calculates an MTI filter matrix "W" by using Expression (2) presented below.

$$W = V \begin{pmatrix} 0 & & & & \\ & 0 & & & \\ & & \ddots & & \\ & & & 1 & \\ & & & & 1 \end{pmatrix} V^H \qquad (2)$$

In Expression (2), "$V^H$" denotes a complex conjugate transpose matrix of "V". Further, on the right-hand side of Expression (2), the matrix between "V" and "$V^H$" is a diagonal matrix having L lines and L columns. From Expression (2), the MTI filter matrix "W" is a matrix having L lines and L columns. In this situation, the value by which the rank is to be reduced is determined by how many diagonal elements in the diagonal matrix having the L lines and the L columns are to be changed to "0". In the following sections, the value by which the rank is to be reduced will be referred to as a "Rank Cut Value".

A column vector (an eigenvector) having a large eigenvalue corresponds to a clutter component that has a small frequency shift caused by the Doppler effect, i.e., that has low moving velocity, in a Doppler scanned range. According to Expression (2), a matrix is calculated by reducing the rank of the matrix "V" by eliminating as many components as the Rank Cut Value starting with components having larger eigenvalues and further inversely transforming the matrix by using "$V^H$". By using Expression (2), it is possible to obtain the MTI filter matrix "W" that functions as a high-pass filter to eliminate moving components (the clutter component) of the tissue.

In this situation, for example, the Doppler processing circuitry 140 determines the Rank Cut Value on the basis of a value set in advance or a value designated by the operator. In the manner described above, the adaptive MTI filter is generated. Further, the Doppler processing circuitry 140 is configured to obtain the blood flow information by inputting the data sequences to the generated adaptive MTI filter. Further, the image generating circuitry 150 is configured to generate the Doppler image data on the basis of the blood flow information obtained by the Doppler processing circuitry 140.

Next, an example of processes performed by the analyzing circuitry 190 according to the first embodiment will be explained. In this situation, an example will be explained in which pieces of Doppler data in a time series (hereinafter, simply, "the Doppler data in the time series") acquired by the first ultrasound scans are stored in the image memory 160, and subsequently, the Doppler data in the time series is read from the image memory 160, so that the analyzing circuitry 190 performs an off-line process on the Doppler data in the time series. The Doppler data in the time series subject to the off-line process is Doppler data corresponding to a region including plaque formed in the carotid artery of the patient P and rendering a blood flow in the plaque. In other words, the Doppler data in the time series is obtained by inputting the received data sequence to an adaptive MTI filter generated on the basis of the received data sequence, the received data sequence being acquired by performing an ultrasound scan multiple times in the frame direction during which an ultrasound wave is transmitted and received once with respect to each of the scanning lines in the region including the plaque, so that the received data sequence includes a plurality of pieces of received data in mutually the same position in the region including the plaque. In this situation, the plaque is an example of the analysis target. A contrast agent may be injected in the patient P to enhance sensitivity. Further, the Doppler data in the time series is, for example, Doppler data corresponding to a plurality of heartbeats.

First, the obtaining function 190*a* in the analyzing circuitry 190 obtains the Doppler data in the time series from the image memory 160. After that, the analyzing function 190*b* in the analyzing circuitry 190 analyzes the Doppler data in the time series and generates a distribution (a first distribution) indicating temporal changes in a blood flow signal intensity level (a first blood flow signal intensity level) in a region of interest (an analysis Region Of Interest [ROI]) including the blood flow in the plaque. In this situation, the distribution (the first distribution) is information (distribution information) indicating the distribution of the temporal changes in the first blood flow signal intensity level. The distribution information hereinafter may simply be referred to as a "distribution".

An example of processes performed by the analyzing function 190*b* will be explained. The analyzing function 190*b* causes the display 103 to display a Doppler image represented by the Doppler image data based on the Doppler data. In this situation, the display 103 displays Doppler images in the order of the time series so as to display a moving picture of the Doppler images. In the following explanations, power image data will be used as an example of the Doppler image data; however, possible examples of the Doppler image data are not limited to this example.

Figure 4:
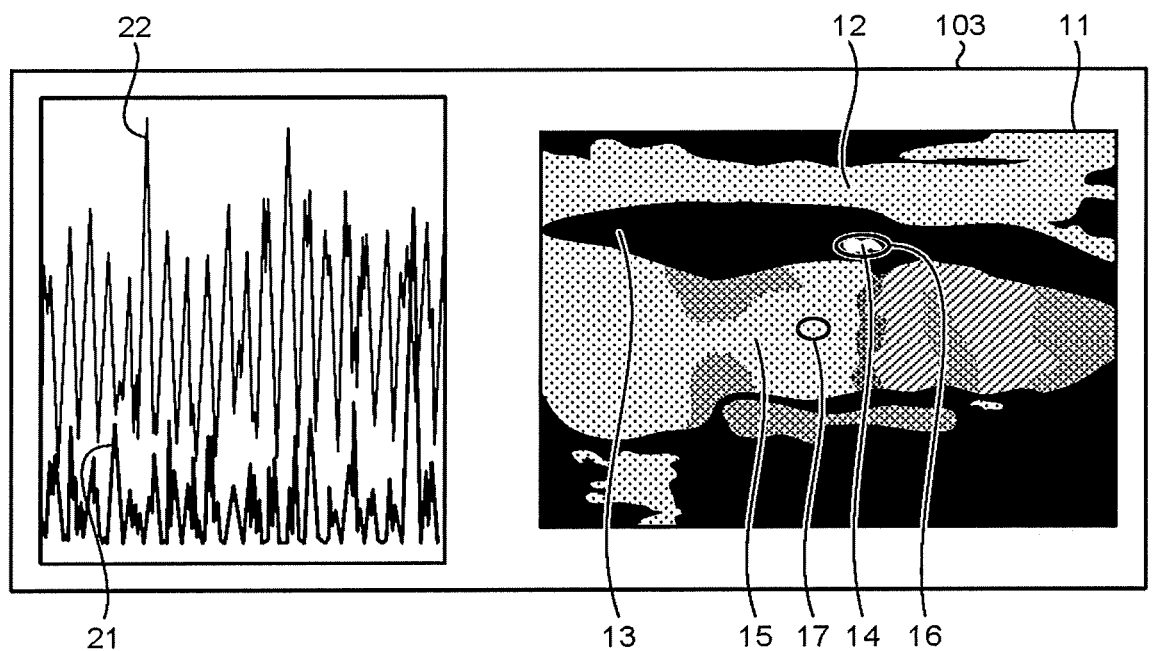
FIG. 4 is a drawing for explaining examples of processes performed by an analyzing function according to the first embodiment.

FIGS. 4 to 8 are drawings for explaining an example of the processes performed by the analyzing function 190*b* according to the first embodiment. The analyzing function 190*b* transmits the Doppler data in the time series to the image generating circuitry 150 and causes the image generating circuitry 150 to generate power image data in a time series, based on the Doppler data in the time series. After that, the analyzing function 190*b* obtains the power image data in the time series from the image generating circuitry 150 and, as illustrated in FIG. 4, causes the display 103 to display a moving picture of power images 11 (Doppler images) 11 based on the power image data in the time series.

Each of the power images 11 renders plaque 13 formed on an inner wall 12 of the carotid artery. In FIG. 4, the plaque 13 corresponds to the part indicated with solid black. Further, the power image 11 renders a blood flow 14 in the plaque 13. Also, the power image 11 also renders the carotid artery and a blood flow (excluding the blood flow 14 in the plaque 13) 15 in the carotid artery.

In this situation, a region of interest (a first region of interest) 16 is set so as to include at least a part of the blood flow 14. The region of interest 16 is manually set as a result of the user operating the input device 102, while one of the plurality of power images 11 designated by the user is being displayed as a still image on the display 103. Alternatively, the analyzing function 190*b* may automatically set the region of interest 16. For example, the analyzing function 190*b* extracts the region of the plaque 13 from the power image data, by performing a binarization process on the power image data representing the power image 11. After that, the analyzing function 190*b* identifies such a region within the region of the plaque 13 that has power values higher than a predetermined threshold value as the region of the blood flow 14 in the plaque 13. After that, the analyzing function 190*b* sets the contour of the region of the blood flow 14 as the region of interest 16.

Further, another region of interest (a second region of interest) 17 is set so as to include at least a part of the blood flow 15 in the carotid artery. Similarly to the region of interest 16, the region of interest 17 is set either manually or automatically. In this situation, within each of the power images 11 other than the power image 11 in which the regions of interest 16 and 17 have been set, the analyzing function 190*b* sets the regions of interest 16 and 17 in such positions that correspond to the positions of the regions of interest 16 and 17 in the power image 11 set with the regions of interest 16 and 17.

When the region of interest 16 has been set, the analyzing function 190*b* generates power values in a time series in the region of interest 16, on the basis of the Doppler data in the time series. In this situation, the analyzing function 190*b* identifies the power values in the position of the region of interest 16 set in the power images 11, with respect to all the pieces of Doppler data in the time series. The power values in the time series in the region of interest 16 represent a distribution (the first distribution) 21 indicating temporal changes in the signal intensity level (the first blood flow signal intensity level) of the blood flow 14 in the region of interest 16. Further, as illustrated in FIG. 4, the controlling circuitry 180 causes the display 103 to display the distribution 21, while the horizontal axis expresses time, whereas the vertical axis expresses the signal intensity levels indicated by the power values.

In this situation, the signal intensity levels of the blood flow in the plaque (e.g., signal intensity levels of the blood flow on the lumen side) serve as an index of easiness for the plaque to come off. For this reason, the distribution 21 is information that makes it possible for the user such as a medical doctor to easily judge the state of the plaque.

Further, when the region of interest 17 has been set, the analyzing function 190*b* generates power values in a time series in the region of interest 17, on the basis of the Doppler data in the time series. The power values in the time series in the region of interest 17 are represented by a distribution (a fourth distribution) 22 indicating temporal changes in a signal intensity level (a second blood flow signal intensity level) of the blood flow 15 in the region of interest 17. Further, as illustrated in FIG. 4, the controlling circuitry 180 causes the display 103 to display the distribution 22, while the horizontal axis expresses time, whereas the vertical axis expresses the signal intensity levels indicated by the power values. In this manner, the analyzing function 190*b* is configured to analyze the Doppler data in the time series and to generate the distribution 22 indicating the temporal changes in the signal intensity level of the blood flow 15 in the region of interest 17 including the blood flow 15 in the carotid artery. In this situation, for example, heartbeats exhibited by the blood flow 15 in the carotid artery are in synchronization with heartbeats exhibited by the blood flow 14 in the plaque 13.

Figure 5:
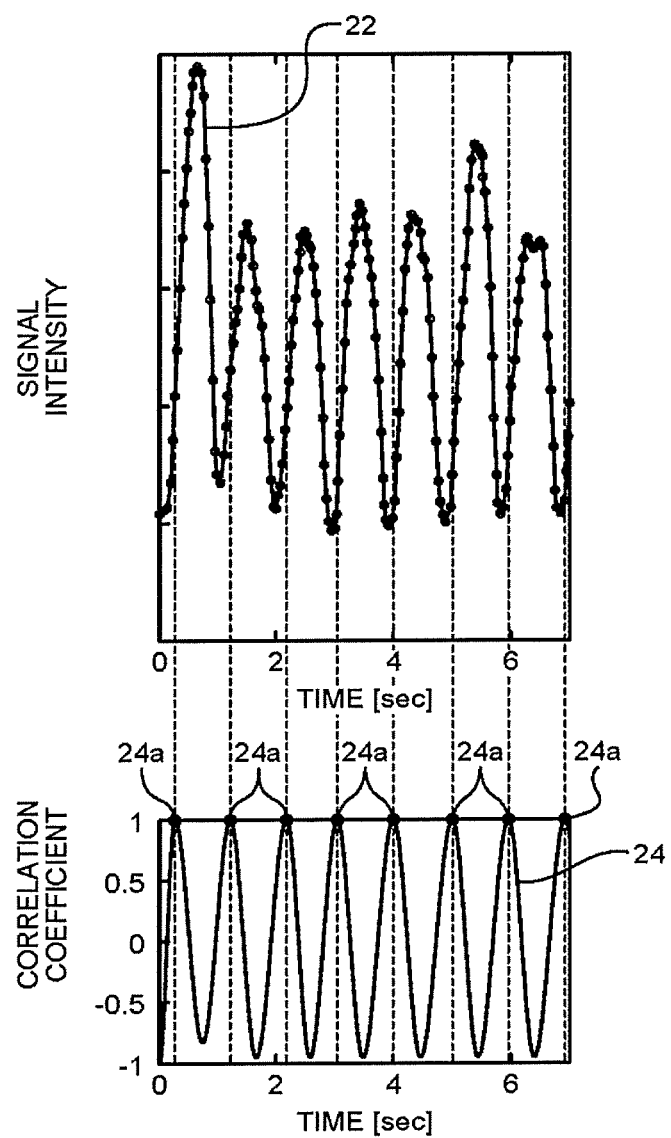
FIG. 5 is a drawing for explaining another example of the processes performed by the analyzing function according to the first embodiment.
Figure 6:
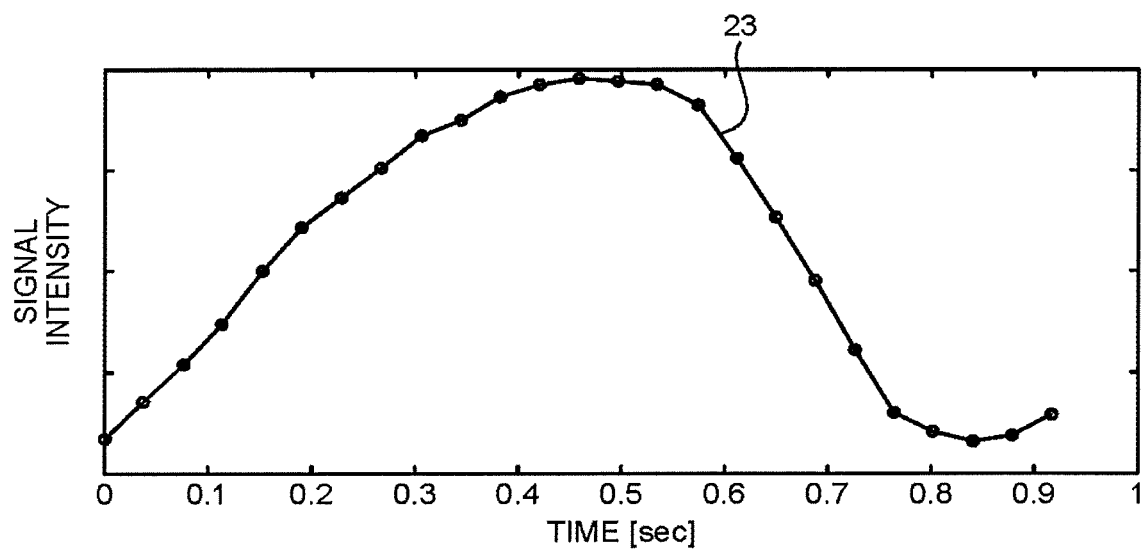
FIG. 6 is a drawing for explaining yet another example of the processes performed by the analyzing function according to the first embodiment.

Further, from the distribution 22 illustrated in FIGS. 4 and 5, the analyzing function 190b cuts out, as illustrated in FIG. 6, a distribution 23 having a predetermined time width (approximately 0.92 [sec] in the example in FIG. 6) used as a reference for one heartbeat. Further, while varying the lag, which is the shift of the distribution 23 in the time direction from the distribution 22, the analyzing function 190b calculates correlation coefficients between the distribution 22 and the distribution 23, so as to calculate a correlation coefficient distribution 24 as illustrated in FIG. 5 in which the horizontal axis expresses time, whereas the vertical axis expresses values of the correlation coefficient. The correlation coefficient is an index value indicating similarity in such a manner that the closer the value thereof is to 1.0, the more similar are the waveform of the distribution 22 and the waveform of the distribution 23.

In the correlation coefficient distribution 24, inflection points 24a at which the correlation coefficient becomes close to 1.0 appear in substantially regular cycles. The analyzing function 190b calculates the time interval between two inflection points 24a next to each other in the time direction, with respect to every pair of inflection points 24a that are next to each other. Further, the analyzing function 190b calculates either an average value or a median value of the calculated plurality of time intervals, as a cyclic period of one heartbeat of the patient P. In this manner, on the basis of the correlation coefficient distribution 24 calculated on the basis of the distribution 22, the analyzing function 190b identifies the cyclic period of one heartbeat. In other words, on the basis of the distribution 22, the analyzing function 190b identifies the cyclic period of one heartbeat.

After that, in correspondence with each cyclic period of one heartbeat that was identified, the analyzing function 190b cuts out a distribution (a second distribution) 25 (see FIG. 7) indicating temporal changes in the signal intensity level (the first blood flow signal intensity level) of the blood flow 14 in the region of interest 16, from the distribution 21. In this manner, from the distribution 21, the analyzing function 190b cuts out a plurality of distributions 25 each having a time width corresponding to the cyclic period of one heartbeat. In other words, the analyzing function 190b obtains the plurality of distributions 25 by dividing the distribution 21 into sections.

Similarly, in correspondence with each cyclic period of one heartbeat that was identified, the analyzing function 190b cuts out a distribution (a fifth distribution) 26 (see FIG. 7) indicating temporal changes in the signal intensity level (the second blood flow signal intensity level) of the blood flow 15 in the region of interest 17, from the distribution 22. In this manner, from the distribution 22, the analyzing function 190b cuts out a plurality of distributions 26 each having a time width corresponding to the cyclic period of one heartbeat. In other words, the analyzing function 190b obtains the plurality of distributions 26 by dividing the distribution 22 into sections.

In this situation, the analyzing function 190b may cause the display 103 to display the plurality of distributions 25 and the plurality of distributions 26.

Figure 8:
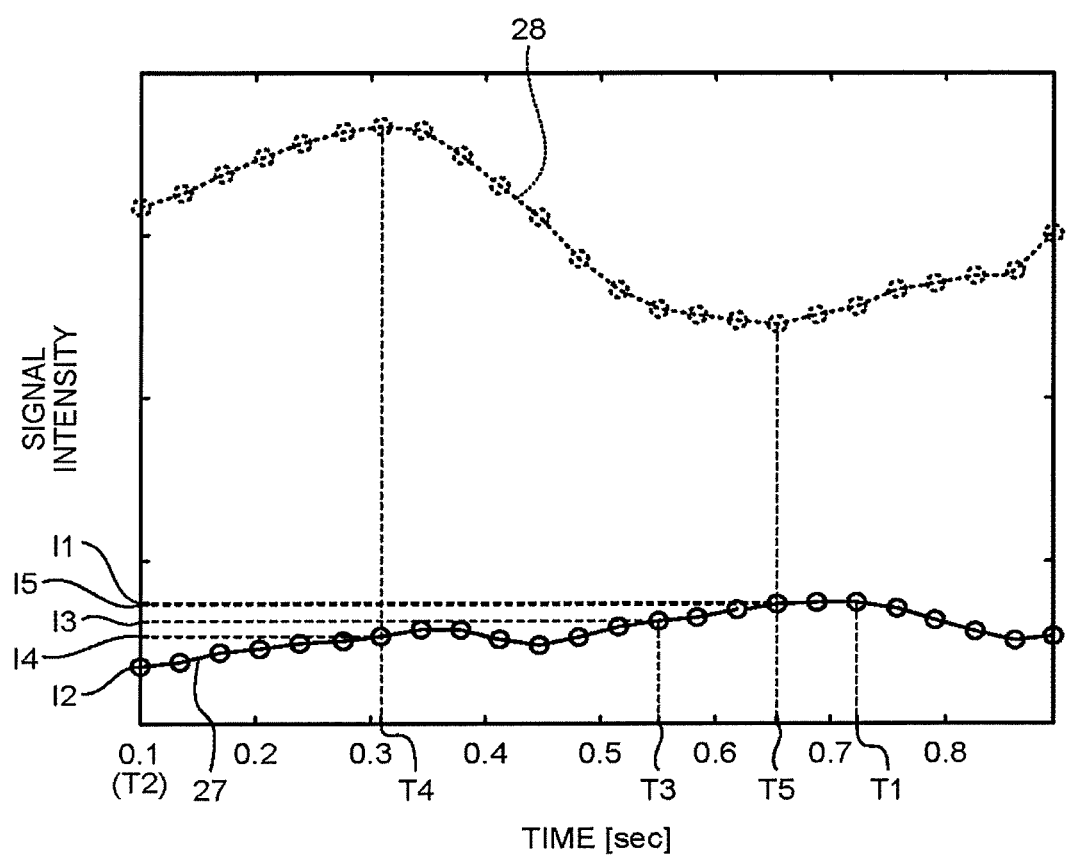
FIG. 8 is a drawing for explaining yet another example of the processes performed by the analyzing function according to the first embodiment.

Further, as illustrated in FIG. 8, the analyzing function 190b generates either an average value or a median value of the plurality of distributions 25 as a distribution (a third distribution) 27 indicating temporal changes in the signal intensity level of the blood flow 14 in the region of interest 16 corresponding to the cyclic period of one heartbeat. In other words, the analyzing function 190b generates the distribution 27 in which the horizontal axis expresses time, whereas the vertical axis expresses the signal intensity levels by performing a smoothing process on the plurality of distributions 25. By performing the smoothing process in this manner, for example, it is possible to suppress impacts of one or more abnormal distributions 25 caused by noise or the like among the plurality of the distributions 25. In this situation, the distribution 27 is also a graph (a first graph) indicating the temporal changes in the signal intensity level of the blood flow 14 in the region of interest 16 corresponding to one heartbeat. In this manner, the analyzing function 190b generates the first graph on the basis of the plurality of distributions 25 calculated on the basis of the distribution 21. In other words, on the basis of the distribution 21, the analyzing function 190b generates the first graph. As explained above, the analyzing function 190b generates a statistical value such as the average value or the median value of the plurality of distributions 25 as the distribution 27. Further, the analyzing function 190b generates the distribution 27 by combining together the plurality of distributions 25 obtained by analyzing the Doppler data corresponding to the plurality of heartbeats and dividing the distribution 21 into the sections.

Similarly, as illustrated in FIG. 8, the analyzing function 190b generates either an average value or a median value of the plurality of distributions 26 as a distribution (a sixth distribution) 28 indicating temporal changes in the signal intensity level of the blood flow 15 in the region of interest 17 corresponding to the cyclic period of one heartbeat. In other words, the analyzing function 190b generates the distribution 28 in which the horizontal axis expresses time, whereas the vertical axis expresses the signal intensity levels by performing a smoothing process on the plurality of distributions 26. In this situation, the distribution 28 is also a graph (a second graph) indicating the temporal changes in the signal intensity level of the blood flow 15 in the region of interest 17 corresponding to one heartbeat. In this manner, the analyzing function 190b generates the second graph on the basis of the plurality of distributions 26 generated on the basis of the distribution 22. In other words, on the basis of the distribution 22, the analyzing function 190b generates the second graph. As explained above, the analyzing function 190b generates a statistical value such as the average value or the median value of the plurality of distributions 26 as the distribution 28. Further, the analyzing function 190b generates the distribution 28 by combining together the plurality of distributions 26 obtained by analyzing the Doppler data corresponding to the plurality of heartbeats and dividing the distribution 22 into the sections.

Further, the controlling circuitry 180 causes the display 103 to display the distribution 27 and the distribution 28. In this situation, the distribution 27 is information that makes it possible for the user such as a medical doctor to easily judge the state of the plaque.

Further, the analyzing function 190b calculates various types of index values that serve as information that makes it possible for the user to easily judge the state of the plaque. For example, the analyzing function 190b calculates an index value based on the temporal changes in the signal intensity level (the first blood flow signal intensity level) of the blood flow 14 in the region of interest 16. As the index value, the analyzing function 190b calculates an index value related to the possibility of the plaque 13 coming off the inner wall 12. The inner wall 12 is an example of the blood vessel wall. The analyzing function 190b calculates the index value per heartbeat. The index value indicates, for example, activeness of the carotid artery. For example, as an index value, the analyzing function 190b identifies a maximum value I1 of the signal intensity in the distribution 27. Alternatively, the analyzing function 190b may identify a minimum value I2 of the signal intensity in the distribution 27, as an index value. In the example in FIG. 8, the value of the signal intensity at a time T1 is the maximum value I1 of the signal intensity, whereas the value of the signal intensity at a time T2 is the minimum value I2 of the signal intensity.

Further, as an index value, the analyzing function 190b may calculate either a ratio or a difference between the maximum value I1 of the signal intensity and the minimum value I2 of the signal intensity. For example, as the ratio between the maximum value I1 of the signal intensity and the minimum value I2 of the signal intensity, the analyzing function 190b may calculate the value (I1/I2) obtained by dividing the maximum value I1 of the signal intensity by the minimum value I2 of the signal intensity or the value (I2/I1) obtained by dividing the minimum value I2 of the signal intensity by the maximum value I1 of the signal intensity.

Further, as the difference between the maximum value I1 of the signal intensity and the minimum value I2 of the signal intensity, the analyzing function 190b may calculate the value (I1−I2) obtained by subtracting the minimum value I2 of the signal intensity from the maximum value I1 of the signal intensity or the value (I2−I1) obtained by subtracting the maximum value I1 of the signal intensity from the minimum value I2 of the signal intensity.

Further, as an index value, the analyzing function 190b may calculate the value ((I1−I3)/T) obtained by calculating the difference (I1−I3) between the maximum value I1 of the signal intensity in the distribution 27 and a value I3 of the signal intensity at a time T3 earlier than the time T1 corresponding to the maximum value I1 by a predetermined length of time T (e.g., 0.2 [sec]) and further dividing the difference (I1−I3) by the predetermined length of time T.

Further, as an index value, the analyzing function 190b may calculate a value indicating a slope of the first graph (the distribution 27) per unit time period (e.g., 1 second). For example, when calculating the abovementioned value ((I1−I3)/T) as an index value, the analyzing function 190b is able to calculate the index value indicating the slope of the first graph per unit time period, by using the predetermined length of time T as the unit time period.

Further, as an index value, the analyzing function 190b may calculate a value of the area defined by the first graph (the distribution 27) and the horizontal axis of the first graph in a predetermined time span. The predetermined time span may be, for example, a span from the start to the end of the cyclic period of one heartbeat. However, possible examples of the predetermined time span are not limited to this example. The predetermined time span may be an arbitrary time span.

Further, as illustrated in FIG. 8, the analyzing function 190b may identify a temporal phase T4 in which the signal intensity in the distribution 28 is at maximum and may calculate, as an index value, a signal intensity value I4 by identifying the value I4 of the signal intensity of the blood flow 14 in the region of interest 16 in the identified temporal phase T4.

Further, as illustrated in FIG. 8, the analyzing function 190b may identify a temporal phase T5 in which the signal intensity in the distribution 28 is at minimum and may calculate, as an index value, a signal intensity value I5 by identifying the value I5 of the signal intensity of the blood flow 14 in the region of interest 16 in the identified temporal phase T5.

Further, as an index value, the analyzing function 190b may calculate, with respect to the power image data in the time series, a ratio between the size of the plaque region and the size of the blood flow region in the plaque. For example, with respect to each of the pieces of power image data, the analyzing function 190b extracts the region of the plaque 13 from the piece of power image data by performing a binarization process on the piece of power image data. After that, the analyzing function 190b identifies such a region within the region of the plaque 13 that has power values higher than a predetermined threshold value, as the region of the blood flow 14 in the plaque 13. After that, the analyzing function 190b calculates the number of pixels in the region of the plaque 13 as a size (an area) Sp of the region of the plaque 13. Also, the analyzing function 190b calculates the number of pixels in the region of the blood flow 14 in the plaque 13 as a size Sb of the region of the blood flow 14. After that, with respect to each of the pieces of power image data, the analyzing function 190b calculates, as an index value, either the value (Sp/Sb) obtained by dividing the size Sp of the region of the plaque 13 by the size Sb of the region of the blood flow 14 or the value (Sb/Sp) obtained by dividing the size Sb of the region of the blood flow 14 by the size Sp of the region of the plaque 13. In this manner, as index values in a time series, the analyzing function 190b calculates ratios (ratios in a time series) between the sizes of the plaque region and the sizes of the blood flow region in the plaque.

By using the method described above, the analyzing function 190b generates the various types of index values on the basis of the distribution 21 described above. Further, the controlling circuitry 180 causes the display 103 to display the various types of index values.

Figure 9:
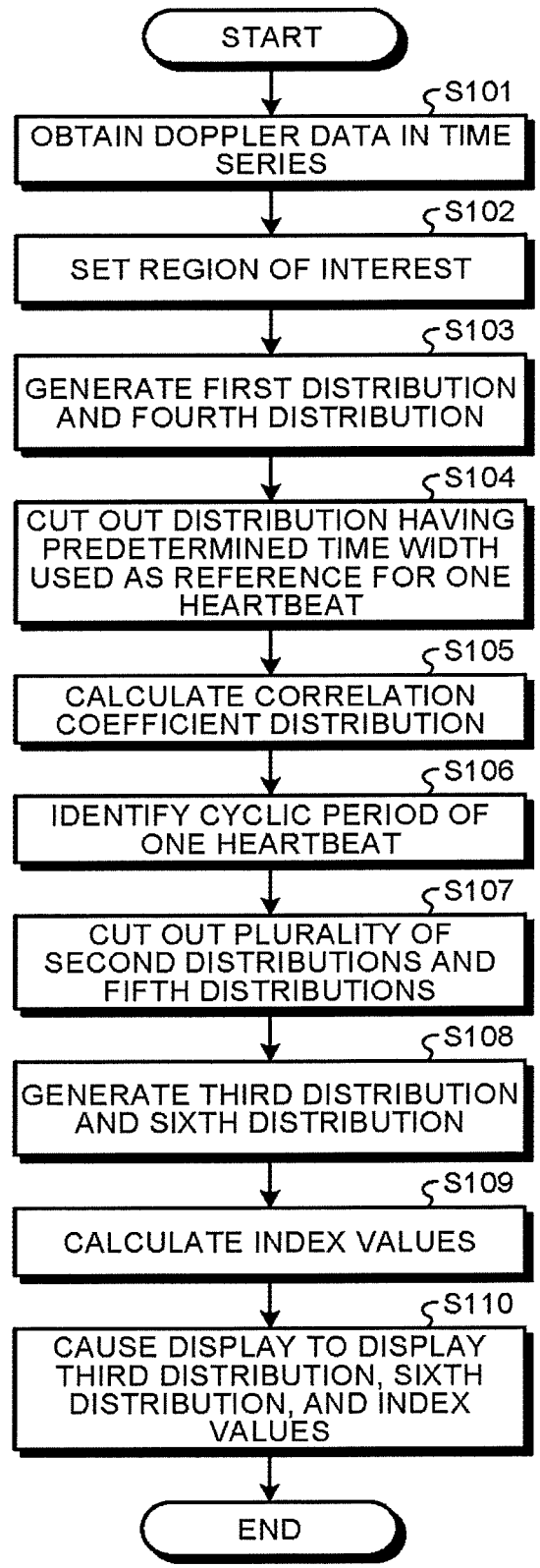
FIG. 9 is a flowchart for explaining an example of a flow in an analyzing process performed by controlling circuitry and analyzing circuitry according to the first embodiment.

Next, with reference to FIG. 9, an example of a flow in an analyzing process performed by the controlling circuitry 180 and the analyzing circuitry 190 will be explained. FIG. 9 is a flowchart for explaining the example of the flow in the analyzing process performed by the controlling circuitry 180 and the analyzing circuitry 190 according to the first embodiment. In this situation, the analyzing process is performed when an instruction to perform the analyzing process is received from the user by the input device 102, while the Doppler data in the time series acquired by the first ultrasound scans described above are stored in the image memory 160.

As illustrated in FIG. 9, the obtaining function 190a included in the analyzing circuitry 190 obtains the Doppler data in the time series from the image memory 160 (step S101). After that, the analyzing function 190b included in the analyzing circuitry 190 sets the region of interest 16 so as to include at least a part of the blood flow 14 in the plaque 13 (step S102). Further, as step S102, the analyzing function 190b sets the region of interest 17 so as to include at least a part of the blood flow 15 in the carotid artery.

Subsequently, on the basis of the Doppler data in the time series, the analyzing function 190b generates the distribution (the first distribution) 21 indicating the temporal changes in the signal intensity level of the blood flow 14 in the region of interest 16 (step S103). Further, at step S103, on the basis of the Doppler data in the time series, the analyzing function 190b generates the distribution (the fourth distribution) 22 indicating the temporal changes in the signal intensity level of the blood flow 15 in the region of interest 17.

Further, the analyzing function 190b cuts out the distribution 23 having the predetermined time width used as a reference for one heartbeat (step S104). After that, the analyzing function 190b calculates the correlation coefficient distribution 24, by calculating the correlation coefficients between the distribution 22 and the distribution 23, while varying the lag, which is the shift of the distribution 23 in the time direction from the distribution 22 (step S105).

Subsequently, on the basis of the correlation coefficient distribution 24, the analyzing function 190b identifies the cyclic period of one heartbeat (step S106). After that, the analyzing function 190b cuts out the plurality of distributions 25 each having the time width corresponding to the cyclic period of one heartbeat, from the distribution 21 (step S107). Further, at step S107, the analyzing function 190b cuts out the plurality of distributions 26 each having the time width corresponding to the cyclic period of one heartbeat from the distribution 22.

On the basis of the plurality of distributions 25, the analyzing function 190b generates the distribution (the third distribution) 27 (step S108). Further, at step S108, the analyzing function 190b generates the distribution (the sixth direction) 28 on the basis of the plurality of distributions 26.

After that, the analyzing function 190b calculates the index values (step S109). Further, the controlling circuitry 180 causes the display 103 to display the distribution 27, the distribution 28, and the index values (step S110) and ends the analyzing process. In other words, at step S110, the controlling circuitry 180 causes the display 103 to display the results of generating the various types of distributions or the like and the results of calculating the various types of index values or the like.

The ultrasound diagnosis apparatus 1 according to the first embodiment has thus been explained. In the first embodiment, as explained above, the various types of distributions and the various types of index values are generated, which make it possible for the user to easily judge the state of the plaque. For example, in the first embodiment, the various types of distributions and the various types of index values are generated, which make it possible for the user to easily judge easiness for the plaque to come off. Consequently, by using the ultrasound diagnosis apparatus 1 according to the first embodiment, it is possible to generate the information that makes it possible for the user to easily judge the state of the plaque.

Further, according to the first embodiment, because the various types of distributions and the various types of index values are displayed on the display, it is possible to enable the user to easily judge the state of the plaque. For example, according to the first embodiment, it is possible to enable the user to easily determine a degree of easiness for the plaque to come off and to easily assess the risk of the plaque coming off.

Further, in the first embodiment, as long as it is possible to estimate the blood flow information about a small blood flow in the plaque, it is also acceptable to use a color Doppler mode or a power Doppler mode, as the image taking mode.

First Modification Example of First Embodiment

In the first embodiment, the example is explained in which the analyzing function 190b identifies the cyclic period of one heartbeat on the basis of the correlation coefficient distribution 24 calculated on the basis of the distribution 22. However, another arrangement is also acceptable in which the analyzing function 190b identifies the cyclic period of one heartbeat on the basis of a correlation coefficient distribution calculated on the basis of the distribution 21. Thus, this modification example will be explained as a first modification example of the first embodiment.

In the first modification example of the first embodiment, the analyzing function 190b cuts out a distribution (hereinafter "cut-out distribution") having the predetermined time width used as a reference for one heartbeat, from the distribution 21 illustrated in FIG. 4, by using the same method as used above for cutting out the distribution 23. After that, the analyzing function 190b calculates the correlation coefficient distribution by calculating correlation coefficients between the distribution 21 and the cut-out distribution, while varying the lag, which is the shift of the cut-out distribution in the time direction from the distribution 21.

In the correlation coefficient distribution, inflection points at which the correlation coefficient becomes close to 1.0 appear in substantially regular cycles. The analyzing function 190b calculates the time interval between two inflection points next to each other in the time direction, with respect to every pair of inflection points that are next to each other. Subsequently, the analyzing function 190b calculates either an average value or a median value of the calculated plurality of time intervals as the cyclic period of one heartbeat of the patient P. In this manner, the analyzing function 190b identifies the cyclic period of one heartbeat, on the basis of the correlation coefficient distribution calculated on the basis of the distribution 21. In other words, the analyzing function 190b identifies the cyclic period of one heartbeat on the basis of the distribution 21.

Second Modification Example of First Embodiment

In the first embodiment, the example is explained in which the analyzing function 190b generates the distribution 27 by using all the distributions 25 cut out from the distribution 21. However, another arrangement is acceptable in which the analyzing function 190b generates the distribution 27 by using one or more of the distributions 25, without using all of the distributions 25 cut out from the distribution 21. For example, when generating the distribution 27, the analyzing function 190b may be configured not to use such distributions 25 that have low reproducibility. Thus, this embodiment will be explained as a second modification example of the first embodiment.

For example, in the second modification example of the first embodiment, the analyzing function 190b calculates a degree of reproducibility by using an evaluation mathematical function such as a reproducibility function to calculate the degree of reproducibility on each of the distributions 25. After that, the analyzing function 190b generates a distribution 27 by using such distributions 25 that each have a degree of reproducibility equal to or higher than a threshold value, without using such distributions 25 that each have a degree of reproducibility lower than the threshold value. In other words, the analyzing function 190b generates the distribution 27 on the basis of such distributions 25 that each meet the predetermined condition where the degree of reproducibility is equal to or higher than the threshold value.

Alternatively, the analyzing function 190b may generate a distribution 27 by using such distributions 25 of which the correlation coefficient described above is equal to or larger than a threshold value, without using such distributions 25 of which the correlation coefficient is smaller than the threshold value. In other words, the analyzing function 190*b* may generate the distribution 27 on the basis of such distributions 25 that each meet the predetermined condition where the correlation coefficient is equal to or larger than the threshold value.

Figure 7:
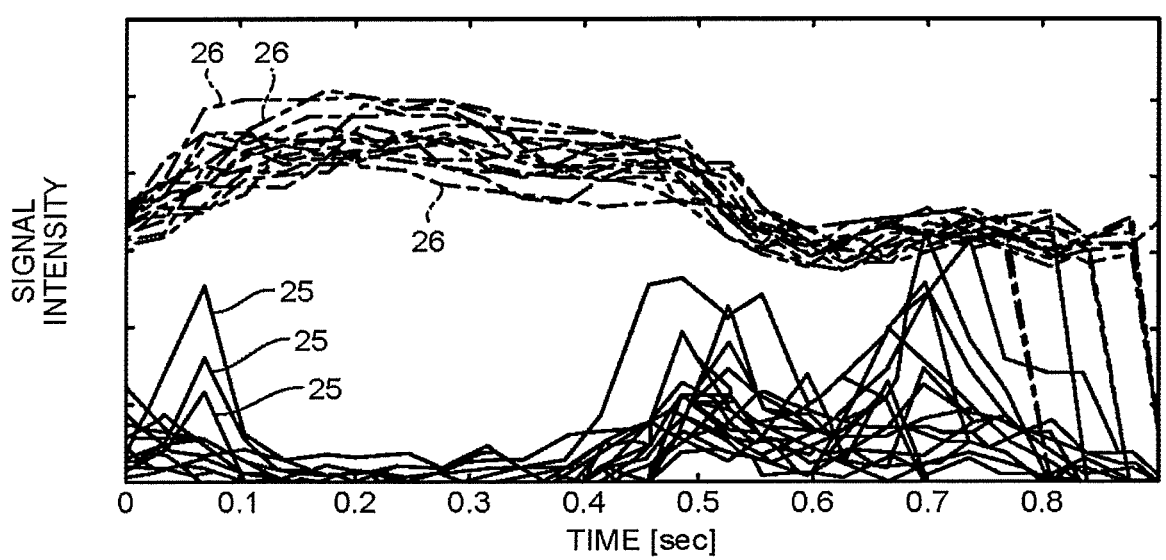
FIG. 7 is a drawing for explaining yet another example of the processes performed by the analyzing function according to the first embodiment.

In another example, for instance, the analyzing function 190*b* may identify the highest signal intensity level of each of all the distributions 25 illustrated in FIG. 7. Further, the analyzing function 190*b* calculates an average value of the highest signal intensity levels, by dividing the sum of the highest signal intensity levels identified from all the distributions 25 by the quantity of the distributions 25.

After that, with respect to each of the distributions 25, the analyzing function 190*b* calculates the difference between the average value of the highest signal intensity levels and the highest signal intensity level of the distribution 25. Subsequently, the analyzing function 190*b* excludes such distributions 25 of which the calculated difference is equal to or larger than a threshold value, when generating a distribution 27. In other words, among all the distributions 25, the analyzing function 190*b* generates the distribution 27 by using only such distributions 25 of which the calculated difference is smaller than the threshold value. In this manner, when generating the distribution 27, the analyzing function 190*b* does not use such distributions 25 that each have low reproducibility. In other words, the analyzing function 190*b* generates the distribution 27 on the basis of such distributions 25 that each meet the predetermined condition where the calculated difference is smaller than the threshold value.

According to the second modification example of the first embodiment, the analyzing function 190*b* generates the distribution 27 without using such distributions 25 that each have low reproducibility, which would lower the level of precision of the distribution 27. Accordingly, it is possible to prevent the level of precision of the distribution 27 from being degraded.

Third Modification Example of First Embodiment

The analyzing function 190*b* may generate an analysis result image (a parametric image) in which colors are assigned in accordance with index values, on the basis of an index value calculated in each of a plurality of positions. Thus, this embodiment will be explained as a third modification example of the first embodiment.

Figure 10:
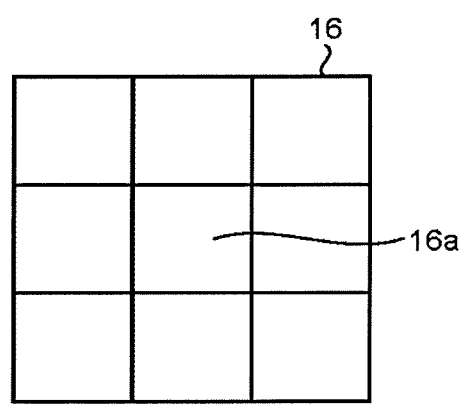
FIG. 10 is a drawing illustrating an example of a region of interest according to a third modification example of the first embodiment.

In the third modification example, for instance, the analyzing function 190*b* moves the region of interest 16 to a plurality of positions in the power image 11 (see FIG. 4), so that the region of interest 16 includes the blood flow 14 in the plaque 13. FIG. 10 is a drawing illustrating an example of the region of interest 16 according to the third modification example of the first embodiment. As illustrated in FIG. 10, the analyzing function 190*b* moves the region of interest 16 made up of 3 pixels by 3 pixels (9 pixels in total) to the plurality of positions in the power image 11 so as to include the blood flow 14 in the plaque 13.

After that, the analyzing function 190*b* calculates the index value described above with respect to each of the positions in the power image 11. Subsequently, for each of the positions, the analyzing function 190*b* determines the calculated index value as an index value corresponding to the position of a center pixel 16*a* of the region of interest 16. After that, the analyzing function 190*b* generates an analysis result image in which a color is assigned in accordance with the index value calculated in each of the plurality of positions. In other words, the analyzing function 190*b* generates the analysis result image in which, on the basis of the index value calculated in each of the plurality of positions, the color corresponding to the index value is assigned. After that, the controlling circuitry 180 causes the display 103 to display the analysis result image. The analysis result image is an example of the image.

In the third modification example, the analysis result image is generated, which makes it easier for the user to intuitively understand the state of the plaque. Consequently, according to the third modification example, it is possible to generate the information that makes it possible for the user to more easily judge the state of the plaque.

Fourth Modification Example of First Embodiment

In the first embodiment, the example was explained in which, after the Doppler data in the time series is stored in the image memory 160, the Doppler data in the time series is read from the image memory 160, so that the analyzing circuitry 190 performs the off-line process on the Doppler data in the time series. However, the analyzing circuitry 190 may perform an on-line process. Thus, this embodiment will be explained as a fourth modification example of the first embodiment.

In the fourth modification example, every time a piece of reflected-wave data is generated by the reception circuitry 110*b*, the Doppler processing circuitry 140 generates a piece of Doppler data on the basis of the reflected-wave data. Further, every time a piece of Doppler data is generated by the Doppler processing circuitry 140, the obtaining function 190*a* and the analyzing function 190*b* included in the analyzing circuitry 190 performs the various types of processes explained above by using the Doppler data. In this manner, in the fourth modification example, the processes are performed in a real-time manner.

Fifth Modification Example of First Embodiment

Next, a fifth modification example of the first embodiment will be explained. In the first embodiment, the example is explained in which the analysis target is the plaque 13 (the blood flow in the plaque 13), so that the analyzing function 190*b* calculates the index value related to the possibility of the plaque 13 coming off the inner wall 12.

However, the analysis target may be a feeding vessel connected to a tumor. For example, in the fifth modification example, the Doppler data in the time series subject to the processing is Doppler data corresponding to a region including a feeding vessel connected to a tumor of the patient P and rendering a blood flow in the feeding vessel.

Further, by performing the same processes as those in the first embodiment on the Doppler data, the analyzing function 190*b* calculates various types of index values related to activeness of the tumor. These index values each serve as information that makes it possible for the user to easily judge the state of the feeding vessel and thereby the state of the tumor.

In another example, the analysis target may be a peripheral blood vessel at a fingertip of the patient P who has diabetes. In that situation, for example, the Doppler data in the time series subject to the processing is Doppler data corresponding to a region including the peripheral blood vessel at the fingertip of the patient P and rendering a blood flow in the peripheral blood vessel.

Further, by performing the same processes as those in the first embodiment on the Doppler data, the analyzing function 190b calculates various types of index values related to activeness of the peripheral blood vessel. These index values each serve as information that makes it possible for the user to easily judge the state of the peripheral blood vessel.

Consequently, according to the fifth modification example, it is possible to generate the information that makes it possible for the user to easily judge the state of the tumor or the peripheral blood vessel of the patient P.

Second Embodiment

Next, a second embodiment will be explained. FIG. 11 is a diagram illustrating an exemplary configuration of a medical image processing apparatus 300 according to the second embodiment. As illustrated in FIG. 11, the medical image processing apparatus 300 is connected to an ultrasound diagnosis apparatus 200 and to an image storing apparatus 400 via a network 500. The configuration illustrated in FIG. 11 is merely an example. Other various types of devices such as terminal devices may be connected to the network 500, besides the ultrasound diagnosis apparatus 200, the image storing apparatus 400, and the medical image processing apparatus 300.

Similarly to the ultrasound diagnosis apparatus 1 explained above, the ultrasound diagnosis apparatus 200 is configured to acquire Doppler data (power data) in a time series and Doppler image data (power image data) in a time series, by performing the first ultrasound scans. Further, the ultrasound diagnosis apparatus 200 is configured to transmit the acquired Doppler data in the time series and the acquired Doppler image data in the time series to the image storing apparatus 400 and to the medical image processing apparatus 300.

The image storing apparatus 400 is configured to store therein the Doppler data in the time series and the Doppler image data in the time series acquired by the ultrasound diagnosis apparatus 200. For example, the image storing apparatus 400 is realized by using a computer apparatus such as a server apparatus. The image storing apparatus 400 is configured to obtain the Doppler data in the time series and the Doppler image data in the time series from the ultrasound diagnosis apparatus 200 via the network 500 and to store the obtained Doppler data in the time series and the obtained Doppler image data in the time series into a memory such as a hard disk, an optical disk, or the like provided inside or outside the apparatus. Further, in response to a request from the medical image processing apparatus 300, the image storing apparatus 400 is configured to transmit any of the Doppler data in the time series and the Doppler image data in the time series stored in the memory, to the medical image processing apparatus 300.

The medical image processing apparatus 300 is configured to obtain the Doppler data in the time series and the Doppler image data in the time series from the ultrasound diagnosis apparatus 200 and from the image storing apparatus 400 via the network 500 and to process the obtained Doppler data in the time series and the obtained Doppler image data in the time series. For example, the medical image processing apparatus 300 obtains the Doppler data in the time series and the Doppler image data in the time series from the ultrasound diagnosis apparatus 200 or from the image storing apparatus 400, further stores the obtained Doppler data in the time series and the obtained Doppler image data in the time series into a memory 320 (explained later), and performs various types of processes on the Doppler data in the time series and the Doppler image data in the time series stored in the memory 320. Further, the medical image processing apparatus 300 is configured to cause a display 340 (explained later) to display various types of distributions and various types of index values resulting from the processes. The medical image processing apparatus 300 is an example of the analyzing apparatus.

As illustrated in FIG. 11, the medical image processing apparatus 300 includes a communication interface 310, the memory 320, an input device 330, the display 340, and processing circuitry 350.

The communication interface 310 is connected to the processing circuitry 350 and is configured to control transferring of various types of data to and from the ultrasound diagnosis apparatus 200 and the image storing apparatus 400 that are connected via the network 500 and to control communication to and from the ultrasound diagnosis apparatus 200 and the image storing apparatus 400. For example, the communication interface 310 is realized by using a network card, a network adaptor, a Network Interface Controller (NIC), or the like. For example, the communication interface 310 is configured to receive the Doppler data in the time series and the Doppler image data in the time series from the ultrasound diagnosis apparatus 200 or from the image storing apparatus 400 and to output the received Doppler data in the time series and the received Doppler image data in the time series to the processing circuitry 350.

The memory 320 is connected to the processing circuitry 350 and is configured to store therein various types of data. For example, the memory 320 is realized by using a semiconductor memory element such as a RAM, a flash memory, or the like, or a hard disk or an optical disk. In the present embodiment, the memory 320 is configured to store therein the Doppler data in the time series and the Doppler image data in the time series received from the ultrasound diagnosis apparatus 200 or from the image storing apparatus 400.

Further, the memory 320 is configured to store therein various types of information used in processes performed by the processing circuitry 350 and processing results and the like obtained by the processing circuitry 350. For example, the memory 320 stores therein display-purpose image data or the like generated by the processing circuitry 350. The memory 320 is an example of a storage unit.

The input device 330 is connected to the processing circuitry 350 and is configured to convert an input operation received from an operator into an electrical signal and to output the electrical signal to the processing circuitry 350. For example, the input device 330 is realized by using a trackball, a switch button, a mouse, a keyboard, a touchpad on which an input operation is performed by touching the operation surface thereof, a touch screen in which a display screen and a touchpad are integrally formed, and/or a contactless input device using an optical sensor, or an audio input device, that are used for establishing various types of settings and the like.

The display 340 is connected to the processing circuitry 350 and is configured to display various types of information and various types of images output from the processing circuitry 350. For example, the display 340 is realized by using a liquid crystal monitor, a Cathode Ray Tube (CRT) monitor, or the like. For example, the display 340 displays a GUI used for receiving an instruction from the operator, various types of display-purpose images, and various types of processing results obtained by the processing circuitry 350. The display 340 is an example of the display unit.

The processing circuitry 350 is configured to control constituent elements of the medical image processing apparatus 300, in response to the input operation received from the operator via the input device 330. For example, the processing circuitry 350 is realized by using a processor. In the present embodiment, the processing circuitry 350 is configured to store the Doppler data in the time series and the Doppler image data in the time series output from the communication interface 310, into the memory 320.

As illustrated in FIG. 11, the processing circuitry 350 includes an obtaining function 351, an analyzing function 352, and a display controlling function 353. In this situation, for example, processing functions of the constituent elements of the processing circuitry 350 illustrated in FIG. 11, namely, the obtaining function 351, the analyzing function 352, and the display controlling function 353, are stored in the memory 320 in the form of computer-executable programs. The processing circuitry 350 realizes the functions corresponding to the programs by reading the programs from the memory 320 and executing the read programs. In other words, the processing circuitry 350 that has read the programs has the functions indicated within the processing circuitry 350 in FIG. 11.

Alternatively, all of the processing functions, namely, the obtaining function 351, the analyzing function 352, and the display controlling function 353, may be stored in the memory 320 in the form of a single computer-executable program. In that situation, the processing circuitry 350 realizes the obtaining function 351, the analyzing function 352, and the display controlling function 353 corresponding to the program, by reading the program from the memory 320 and executing the read program.

The obtaining function 351 corresponds to the obtaining function 190a explained above. The obtaining function 351 is configured to perform the same processes as those performed by the obtaining function 190a, by using the Doppler data in the time series and the Doppler image data in the time series stored in the memory 320. The obtaining function 351 is an example of an obtaining unit.

The analyzing function 352 corresponds to the analyzing function 190b explained above. The analyzing function 352 is configured to perform the same processes as those performed by the analyzing function 190b. The analyzing function 352 is an example of an analyzing unit.

The display controlling function 353 corresponds to the display controlling function of the controlling circuitry 180 explained above. The display controlling function 353 is configured to perform the same processes as those performed by the display controlling function of the controlling circuitry 180. The display controlling function 353 is an example of a display controlling unit.

The medical image processing apparatus 300 according to the second embodiment has thus been explained. Similarly to when using the ultrasound diagnosis apparatus 1 explained above, by using the medical image processing apparatus 300 according to the second embodiment, it is possible to generate the information that makes it possible for the user to easily judge the state of the plaque, the tumor, or the peripheral blood vessel.

According to at least one aspect of the embodiments and modification examples explained above, it is possible to generate the information that makes it possible for the user to easily judge the various states of the patient P.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analyzing apparatus, comprising:
processing circuitry configured to
obtain pieces of Doppler image data in a time series rendering of a blood flow in plaque formed in a blood vessel, the pieces of Doppler image data corresponding to a plurality of heartbeats;
analyze the pieces of Doppler image data in the time series; and
calculate an index value based on temporal changes in a first blood flow signal intensity level in a first region of interest including the blood flow in the plaque by:
generating first distribution information indicating the temporal changes in the first blood flow signal intensity level,
determining particular distribution information having a predetermined time width, the particular distribution information being cut out from the first distribution information,
calculating correlation coefficient distribution information by calculating correlation coefficients between the first distribution information and the particular distribution information, while varying a lag, which is a shift of the particular distribution information from the first distribution information,
determining a cyclic period of one heartbeat using the correlation coefficient distribution information, and
calculating the index value using the determined cyclic period of one heartbeat.

2. The analyzing apparatus according to claim 1, wherein the processing circuitry is further configured to calculate the index value indicating activeness of the blood vessel.

3. The analyzing apparatus according to claim 1, wherein the processing circuitry is further configured to calculate the index value related to a possibility of the plaque coming off a blood vessel wall.

4. The analyzing apparatus according to claim 1, wherein the processing circuitry is further configured to calculate the index value per heartbeat.

5. The analyzing apparatus according to claim 1, wherein the processing circuitry is further configured to generate a first graph indicating the temporal changes in the first blood flow signal intensity level based on the first distribution information.

6. The analyzing apparatus according to claim 5, wherein the processing circuitry is further configured to calculate the index value indicating a slope of the first graph per unit time period.

7. The analyzing apparatus according to claim 1, wherein, based on the index value calculated in each of a plurality of positions, the processing circuitry is further configured to generate an image in which colors are assigned to the index values.

8. The analyzing apparatus according to claim 1, wherein the processing circuitry is further configured to analyze the plurality of pieces of Doppler image data corresponding to the plurality of heartbeats and generate third distribution information by combining together a plurality of pieces of second distribution information obtained by dividing the first distribution information into sections.

9. The analyzing apparatus according to claim 8, wherein, as the index value, the processing circuitry is further configured to calculate either a maximum value or a minimum value of the first blood flow signal intensity level exhibited in the third distribution information.

10. The analyzing apparatus according to claim 8, wherein, as the index value, the processing circuitry is further configured to calculate either a ratio or a difference between a maximum value and a minimum value of the first blood flow signal intensity level exhibited in the third distribution information.

11. The analyzing apparatus according to claim 8, wherein, as the index value, the processing circuitry is further configured to calculate a difference between a maximum value of the first blood flow signal intensity level exhibited in the third distribution information and a value of the first blood flow signal intensity level exhibited at a time earlier than a time of the maximum value by a predetermined length of time and calculate a value obtained by dividing the difference by the predetermined length of time.

12. The analyzing apparatus according to claim 5, wherein
the processing circuitry is further configured to generate the first graph in which a horizontal axis expresses time, whereas a vertical axis expresses the first blood flow signal intensity level, and
the processing circuitry is further configured to calculate, as the index value, a value of an area defined by the first graph and the horizontal axis in a predetermined time span.

13. The analyzing apparatus according to claim 3, wherein, as the index value, the processing circuitry is further configured to calculate a ratio between a size of a region of the plaque and a size of a blood flow region in the plaque, with respect to the pieces of Doppler image data in the time series.

14. The analyzing apparatus according to claim 8, wherein the processing circuitry is further configured to generate the third distribution information indicating temporal changes in the first blood flow signal intensity level corresponding to the determined cyclic period of one heartbeat.

15. The analyzing apparatus according to claim 14, wherein the processing circuitry is further configured to generate the third distribution information by combining together the plurality of pieces of second distribution information obtained by dividing the first distribution information into the sections based on the determined cyclic period of one heartbeat.

16. The analyzing apparatus according to claim 8, wherein the processing circuitry is further configured to generate, as the third distribution information, a statistical value of the plurality of pieces of second distribution information.

17. The analyzing apparatus according to claim 15, wherein the processing circuitry is further configured to generate the third distribution information, based on one or more of the plurality of pieces of second distribution information that meet a predetermined condition.

18. The analyzing apparatus according to claim 1, wherein
the pieces of Doppler image data in the time series further render the blood vessel, and
the processing circuitry is further configured to analyze the pieces of Doppler image data in the time series and generate fourth distribution information indicating temporal changes in a second blood flow signal intensity level in a second region of interest including a blood flow in the blood vessel.

19. The analyzing apparatus according to claim 18, wherein the processing circuitry is further configured to generate a second graph indicating the temporal changes in the second blood flow signal intensity level based on the fourth distribution information.

20. The analyzing apparatus according to claim 18, wherein
the processing circuitry is further configured to analyze the pieces of Doppler image data corresponding to the plurality of heartbeats and generate sixth distribution information by combining together a plurality of pieces of fifth distribution information obtained by dividing the fourth distribution information into sections.

21. The analyzing apparatus according to claim 20, wherein the processing circuitry is further configured to determine a temporal phase in which the second blood flow signal intensity level is at maximum or minimum in the sixth distribution information and calculate, as the index value, a value of the first blood flow signal intensity level in the temporal phase.

22. The analyzing apparatus according to claim 1, wherein the processing circuitry is further configured to cause a display to display the index value.

23. The analyzing apparatus according to claim 5, wherein the processing circuitry is further configured to cause a display to display the first graph.

24. The analyzing apparatus according to claim 1, wherein
the processing circuitry is further configured to analyze the pieces of Doppler image data corresponding to the plurality of heartbeats, generate fourth distribution information indicating temporal changes in a second blood flow signal intensity level in a second region of interest including a blood flow in the blood vessel, determine the cyclic period of one heartbeat based on the fourth distribution information, and generate third distribution information indicating temporal changes in the first blood flow signal intensity level corresponding to the determined cyclic period of one heartbeat.

25. The analyzing apparatus according to claim 1, wherein the processing circuitry is further configured to obtain the pieces of Doppler image data in the time series obtained by inputting a received data sequence to an adaptive Motion Target Indicator (MTI) filter generated based on the received data sequence, the received data sequence being acquired by performing an ultrasound scan multiple times in a frame direction during which an ultrasound wave is transmitted and received once with respect to each of scanning lines in a region including the analysis target, so that the received data sequence includes a plurality of pieces of received data in a mutually same position in the region.

26. The analyzing apparatus according to claim 1, wherein the processing circuitry is further configured to obtain the pieces of Doppler image data in the time series rendering the blood flow in the analysis target formed in the blood vessel of a patient who has a contrast agent injected.

27. An analyzing method, comprising:
obtaining pieces of Doppler image data in a time series rendering of a blood flow in plaque formed in a blood vessel, the pieces of Doppler image data corresponding to a plurality of heartbeats; and
analyzing the pieces of Doppler image data in the time series; and calculating an index value based on temporal changes in a first blood flow signal intensity level in a first region of interest including the blood flow in the plaque by:
  generating first distribution information indicating the temporal changes in the first blood flow signal intensity level,
  determining particular distribution information having a predetermined time width, the particular distribution information being cut out from the first distribution information,
  calculating correlation coefficient distribution information by calculating correlation coefficients between the first distribution information and the particular distribution information, while varying a lag, which is a shift of the particular distribution information from the first distribution information,
  determining a cyclic period of one heartbeat using the correlation coefficient distribution information, and
  calculating the index value using the determined cyclic period of one heartbeat.

28. An analyzing apparatus, comprising:
processing circuitry configured to
  obtain pieces of first Doppler image data in a time series rendering of a blood flow in plaque formed in a blood vessel and pieces of second Doppler image data in the time series rendering of a blood flow outside the plaque, the pieces of the first Doppler image data corresponding to a plurality of heartbeats and the pieces of the second Doppler image data corresponding to the plurality of heartbeats;
  analyze the pieces of the first Doppler image data in the time series; and
  calculate an index value based on temporal changes in a first blood flow signal intensity level in a first region of interest including the blood flow in the plaque by:
    generating first distribution information indicating the temporal changes in the first blood flow signal intensity level and second distribution information indicating temporal changes in a second blood flow signal intensity level in a second region of interest including the blood flow outside the plaque,
    determining particular distribution information having a predetermined time width, the particular distribution information being cut out from the second distribution information,
    calculating correlation coefficient distribution information by calculating correlation coefficients between the second distribution information and the particular distribution information, while varying a lag, which is a shift of the particular distribution information from the second distribution information,
    determining a cyclic period of one heartbeat using the correlation coefficient distribution information, and
    calculating the index value using the determined cyclic period of one heartbeat.

* * * * *